United States Patent
Kim-Whitty

(10) Patent No.: US 10,803,988 B2
(45) Date of Patent: *Oct. 13, 2020

(54) COLOR ANALYSIS AND CONTROL USING A TRANSPARENT DISPLAY SCREEN ON A MOBILE DEVICE WITH NON-TRANSPARENT, BENDABLE DISPLAY SCREEN OR MULTIPLE DISPLAY SCREEN WITH 3D SENSOR FOR TELEMEDICINE DIAGNOSIS AND TREATMENT

(71) Applicant: SK COMMERCIAL CONSTRUCTION, INC., Belton, TX (US)

(72) Inventor: Suk K. Kim-Whitty, Belton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/439,821

(22) Filed: Jun. 13, 2019

(65) Prior Publication Data

US 2019/0311796 A1    Oct. 10, 2019

Related U.S. Application Data

(63) Continuation-in-part of application No. 16/286,443, filed on Feb. 26, 2019, which is a continuation-in-part
(Continued)

(51) Int. Cl.
*G06T 7/90*    (2017.01)
*G16H 30/40*   (2018.01)
(Continued)

(52) U.S. Cl.
CPC .......... *G16H 30/40* (2018.01); *A61B 5/1032* (2013.01); *G06T 1/0007* (2013.01); *G06T 7/90* (2017.01);
(Continued)

(58) Field of Classification Search
CPC ...... G16H 30/40; G16H 30/20; A61L 5/1032; G06T 7/90; G06T 7/0002; G06T 7/40; G06T 2200/24; G06T 2207/10012; G02B 27/017; G02B 27/0172; G02B 2027/0138; G02B 2027/014; G02B 2027/0178
See application file for complete search history.

(56) References Cited

U.S. PATENT DOCUMENTS 10,290,120 B2 *  5/2019  Kim-Whitty ............. G06T 7/90
2004/0116013 A1 * 6/2004  Yoshida ................... B32B 3/10
                                                     442/43
(Continued)

*Primary Examiner* — Yu Chen
(74) *Attorney, Agent, or Firm* — Hulsey P.C.

(57) ABSTRACT

The present disclosure relates to mobile electronic devices including at least one transparent display screen for color analysis and control relating to medical conditions using an electronic mobile device have a transparent display screen and a non-transparent display screen, bendable display screen and multiple screen device with 3D sensor used as telemedicine device. Color data for a perceived color stores in a memory and displays images as perceived through the transparent display screen. Image difference values are determined between a first set of optical processing data and a second set of optical processing data. The transparent display screen indicates image difference values from including differences in color, texture, transparency, lighting, etc., especially for augmented reality applications.

20 Claims, 13 Drawing Sheets

Related U.S. Application Data of application No. 15/635,502, filed on Jun. 28, 2017, now Pat. No. 10,290,120, application No. 16/439,821, filed on Jun. 13, 2019, which is a continuation-in-part of application No. 15/464,231, filed on Mar. 20, 2017, now abandoned, and a continuation-in-part of application No. 15/477,124, filed on Apr. 3, 2017, now Pat. No. 9,967,553, and a continuation-in-part of application No. 15/477,131, filed on Apr. 3, 2017, now Pat. No. 9,801,693, which is a continuation-in-part of application No. 15/477,301, filed on Apr. 3, 2017, now Pat. No. 10,116,924.

(51) Int. Cl.

| | | |
|---|---|---|
| *G16H 30/20* | (2018.01) | |
| *G06T 1/00* | (2006.01) | |
| *G06T 11/60* | (2006.01) | |
| *A61B 5/103* | (2006.01) | |
| *G06T 19/00* | (2011.01) | |
| *G06T 11/00* | (2006.01) | |
| *H04N 7/14* | (2006.01) | |
| *G06T 7/00* | (2017.01) | |
| *G06T 7/529* | (2017.01) | |

(52) U.S. Cl.
CPC ............ *G06T 11/60* (2013.01); *G06T 19/006* (2013.01); *G16H 30/20* (2018.01); *G06T 7/0014* (2013.01); *G06T 7/529* (2017.01); *G06T 11/001* (2013.01); *H04N 7/142* (2013.01); *H04N 2007/145* (2013.01)

(56) References Cited

U.S. PATENT DOCUMENTS

| | | | | |
|---|---|---|---|---|
| 2004/0190019 | A1* | 9/2004 | Li | H04N 1/6033 358/1.9 |
| 2008/0294017 | A1* | 11/2008 | Gobeyn | A61B 5/411 600/301 |
| 2012/0068913 | A1* | 3/2012 | Bar-Zeev | G09G 3/2003 345/8 |
| 2013/0314303 | A1* | 11/2013 | Osterhout | G06F 3/005 345/8 |
| 2015/0002769 | A1* | 1/2015 | Kalyanasundaram | G02F 1/13476 349/33 |
| 2016/0112654 | A1* | 4/2016 | Seo | G01J 3/463 348/333.12 |
| 2016/0155242 | A1* | 6/2016 | Bean | G06T 15/503 345/592 |
| 2016/0240125 | A1* | 8/2016 | Sridharan | G09G 5/06 |
| 2016/0248994 | A1* | 8/2016 | Liu | A61B 5/02055 |
| 2017/0090194 | A1* | 3/2017 | Hayes | G06T 19/006 |
| 2017/0270707 | A1* | 9/2017 | Kass | G06T 19/006 |
| 2018/0033361 | A1* | 2/2018 | Cichonski | G06T 7/90 |
| 2018/0053284 | A1* | 2/2018 | Rodriguez | G06T 3/4007 |
| 2018/0130431 | A1* | 5/2018 | Hwang | G06T 5/40 |
| 2018/0149777 | A1* | 5/2018 | Brown | G02B 5/0278 |
| 2020/0104998 | A1* | 4/2020 | Dacosta | A61B 5/445 |

\* cited by examiner

COLOR ANALYSIS AND CONTROL USING A TRANSPARENT DISPLAY SCREEN ON A MOBILE DEVICE WITH NON-TRANSPARENT, BENDABLE DISPLAY SCREEN OR MULTIPLE DISPLAY SCREEN WITH 3D SENSOR FOR TELEMEDICINE DIAGNOSIS AND TREATMENT

CROSS REFERENCE TO RELATED APPLICATIONS

This application further claims the benefit of the following non-provisional applications, all of which are here expressly incorporated by reference:

Ser. No. 15/464,231 entitled "METHOD AND SYSTEM FOR ADVERTISING AND SCREEN IDENTIFICATION USING A MOBILE DEVICE TRANSPARENT SCREEN," filed on Mar. 20, 2017;

Ser. No. 15/477,124, entitled "ENHANCED TRANSPARENT DISPLAY SCREEN FOR MOBILE DEVICE AND METHODS OF OPERATION," filed on Apr. 3, 2017;

Ser. No. 15/477,301, entitled "COLOR ANALYSIS AND CONTROL USING AN ELECTRONIC MOBILE DEVICE TRANSPARENT DISPLAY SCREEN," filed on Apr. 3, 2017;

Ser. No. 15/635,502, entitled "COLOR ANALYSIS AND CONTROL USING AN ELECTRONIC MOBILE DEVICE TRANSPARENT DISPLAY SCREEN," filed Sep. 20, 2018;

Ser. No. 16/286,443 entitled "COLOR ANALYSIS AND CONTROL USING AN ELECTRONIC MOBILE DEVICE TRANSPARENT DISPLAY SCREEN INTEGRAL WITH THE USE OF AUGMENTED REALITY GLASSES," filed on Feb. 26, 2019; and Ser. No. 15/477,131, entitled "METHOD AND SYSTEM FOR CORRELATING ANATOMY USING AN ELECTRONIC MOBILE DEVICE TRANSPARENT DISPLAY SCREEN," filed on Apr. 3, 2017.

FIELD OF THE INVENTION

The present disclosure relates to mobile electronic devices including at least one transparent display screen for comparing and accurately determining the color of a predetermined object for color and texture application. Particularly, the present disclosure provides a method and system for color analysis and control using a transparent display screen on a mobile device with non-transparent, bendable display screen or multiple display screen with 3d sensor for telemedicine diagnosis and treatment. Moreover, the present disclosure provides color analysis and control using an electronic mobile device transparent display screen, for a wide variety of applications, including, but not limited to color, shade and coating defect identification applications, as well as augmented reality applications. Furthermore, here is provided color and texture analysis with mobile device, transparent and non-transparent display screen with 3D sensor/3D optical camera sensor for accurate recording of visible medical condition to be sent to medical personnel for telemedicine diagnostics.

BACKGROUND OF THE INVENTION

In the use of transparent display screens on mobile electronic device there is the desire to compare colors, shades, textures and other image parameters. The transparent display screen may be a single display layered or multiple display layered, bonded or formed monolithic. The particular electronic mobile device may have single or multiple transparent display screen with capability to have one layer become non-transparent/opaque. In using a transparent display layer, the user may identify, compare shades of color while looking through part of transparent display on a mobile device. The advantage of enabling comparison through transparent display screen is significant. This property exists since the color is shown on part of transparent display screen, as such, colors may be compared by directly compared to other colors or shades of a color using same light source seen through transparent display screen.

Individual perception of subject with color that is being compared will be more similar due to non-camera factors which will affect the results; which also include translucent shades like tinted beverage/fluid seen through glass. Example: looking through glass cup with beverage like dark beer, utilizing comparison shade guide seen through transparent display screen has advantage due to same background/surrounding/environment/lighting/objects seen behind the glass cup and transparent display will be same for more accuracy. Non-transparent display screen has a color "break" due to edge of screen, to include curve edge (which has slight lighting difference at the edges) and viewed camera limits (RGB).

On multiple transparent displays a layered screen, utilizing a transparent display screen to display coating defects in parallax image over the color, for more realistic image comparison. For comparing paint coatings, color identification is not only factor. Other factors include defects associated with coating systems (texture defects on the color), such as alligatoring, bleeding, blistering, checking, fisheyes, etc., which can be better visually shown through transparent display screen in form of overlay as viewed through transparent display screen.

There is the desire to perceive and control these image aspects with a transparent display screen on an electronic mobile device. With such ability, color, shade and coating defect identification and other variations could be appreciated. Such variations and their control could have application in a variety of scenarios, including augmented reality scenarios.

Rapid advances in Mobile Devices and AR/MR/VR Glasses Head Mount Unit (HMU) with transparent and non-transparent screen and 3D sensor/3D optical camera sensor make it possible to accurately capture digital imagery, including dimensional data, of medical anomalies. Patients can then transmit 3D images with color and texture data to their medical practitioner for analysis and initial diagnosis. General Practitioners may forward this data to a Specialist for an improved telemedicine diagnosis.

BRIEF SUMMARY OF THE INVENTION

The disclosed subject matter provides for color analysis and control using an electronic mobile device transparent display screen. Additionally, the present disclosure provides a method and system for operation on a mobile electronic device including at least one transparent display screen for comparing and accurately determining the color of a predetermined object.

In summary, here is provided a method and system for comparing and accurately determining the color of a predetermined human body part using an electronic mobile device comprising at least one transparent display screen, the method and system provide the steps and structures for storing optical processing data and optical processing instructions and algorithms in a memory associated with the electronic mobile device. The disclosed method and system enable operating a computer processor associated with the electronic mobile device for executing said optical processing instructions and algorithms in response to optical processing data generated by the electronic mobile device. The disclosed method and system enable directing an optical lens of the electronic mobile device to capture an image of an human body part for display on at least one transparent display screen of the mobile electronic device, wherein said transparent display screen comprises a head-mounted display in the form of a pair of augmented reality glasses, The disclosed method and system enable collecting a first set of optical processing data using data deriving from the capture of the image through the optical lens of the electronic mobile device, said first set of optical processing data comprising a first set of color data. The disclosed method and system enable displaying the human body part for display through a transparent portion of the at least one transparent display screen of the mobile electronic device. The disclosed method and system enable receiving and storing in the memory a second set of color data associated with a perceived color of the human body part for display as perceived through the at least one transparent display screen. The disclosed method and system enable executing instructions on the computer processor associated with the electronic mobile device determining image difference values between said first set of optical processing data and said second set of optical processing data The disclosed method and system enable displaying on the at least one transparent display screen values for said image differences from the group consisting of color differences, texture differences, transparency differences, lighting differences, motion differences, focus differences and the like. The disclosed method and system enable further enhancing the transparent display screen through collection of various information for feedback with utilization of all sensors to include 3D camera and or 3D sensor The system uses at least one transparent display screen comprises a single display screen having at least one bonded monolithic form or a layered monolithic form. The system further includes optical processing data and optical processing instructions and algorithms for storing in the memory associated with the electronic mobile device and executing on the computer processor associated with the electronic mobile device for controllably varying the translucence of said at least one transparent display screen through a translucence range of zero translucence or opaque to 100% translucence or transparent. The system further includes optical processing data and optical processing instructions and algorithms for storing in the memory associated with the electronic mobile device and executing on the computer processor associated with the electronic mobile device for generating suggestions to a user for determining possible factors causing a color value for said first perceived color of interest to differ from a color value for said second perceived color of interest.

Persons with a visible medical condition may use mobile devices and AR/MR/VR glasses head mount units (HMU) with transparent and non-transparent screen and 3D sensor/3D optical camera sensor to digitally record the medical condition and forward the data to a general practitioner for improved image, color and texture analysis for telemedicine.

Mobile devices and AR/MR/VR glasses head mount units (HMU) with transparent and non-transparent screen and 3D sensor/3D optical camera sensor is used by medical practitioner for telemedicine/medical diagnostic purpose, telemedicine for color and texture analysis quality management system (QMS) is to be established with multiple redundant 3D images from same and different angles for redundancy.

A technical advantage of the present disclosure includes color shade and texture matching including three-dimensional and parallax touchscreen operation which can distinguish pressure differences in touch screen control. Using pressure differences, the perception of texture and depth can be significantly enhanced for uses of the present disclosure.

Another technical advantage of the present disclosure includes the ability to provide to a user options in matching color and texture for various objects with use of different levels of pressure applied to the transparent touch screen of a mobile electronic device. For example, a user can choose texture, but color must be changed or vice versa, with different level of pressure, user can leave texture as is and just change the color. These control variations make the user experience much richer and rewarding, because of the ability to respond to varying levels of pressure on to touch screen.

A further technical advantage of the present disclosure includes the ability to appreciate how objects with same color and different textures may have different perceived color parameters. For example, in considering paint as it dries, color might match but there could be at least 20 different textures it could appear with it. With paint drying or with defects like cracking, fisheye looking defects, peeling and etc., the color matching and analysis system of the present disclosure gives the ability to address such variations.

Another technical advantage of the present disclosure includes the ability to use a parallax image to provide the ability to make more valuable distinctions between colors as a function of the texture of the particular object.

Another technical advantage of the present disclosure incorporates the concept of having dual transparent screens associated with a single mobile electronic device. Dual transparent screens provide the ability to determine various aspects of parallax images to control the way images are collected and may be responded to using multiple transparent screens.

The present disclosure further provides the ability to address texture differences in a three-dimensional screen for a variety of applications, including construction, painting, texture with foods, other aspects of perception where the ability to perceive an image through the transparent screen at the same time associate with the particular textures and other dimensional aspect of the object. This aspect provides the ability through the transparent display screen of perceiving objects characteristics that otherwise it cannot be perceived.

BRIEF DESCRIPTION OF THE DRAWINGS

The present subject matter will now be described in detail with reference to the drawings, which are provided as illustrative examples of the subject matter so as to enable those skilled in the art to practice the subject matter. Notably, the FIGUREs and examples are not meant to limit the scope of the present subject matter to a single embodiment, but other embodiments are possible by way of interchange of some or all of the described or illustrated elements and, further, wherein.

DETAILED DESCRIPTION OF ILLUSTRATIVE EMBODIMENTS

Figure 1:
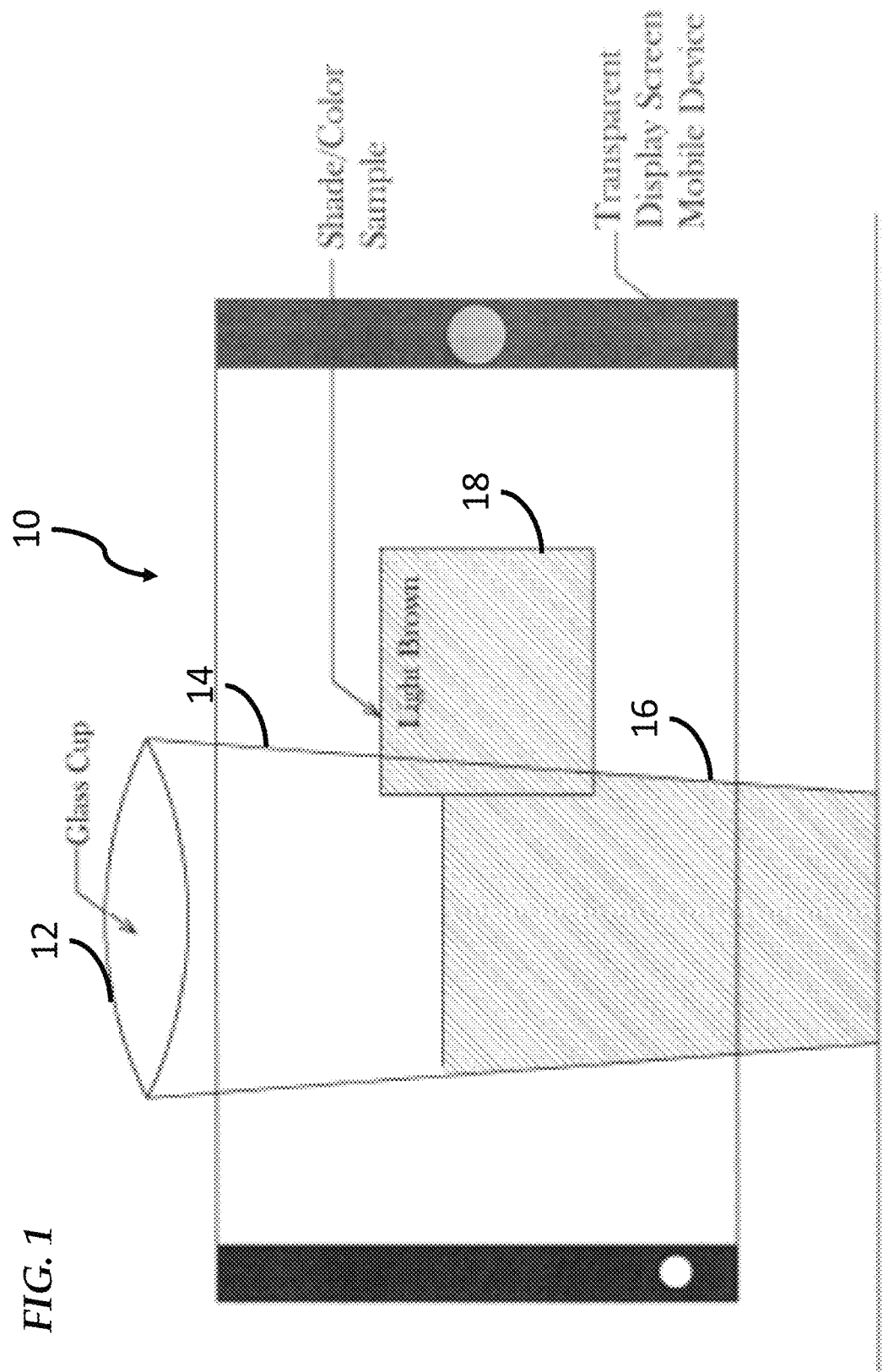
FIG. 1 is a view of an image as seen through a transparent display screen of a mobile electronic device for demonstrating aspects of the present disclosure.

The detailed description set forth below in connection with the appended drawings is intended as a description of exemplary embodiments in which the presently disclosed process can be practiced. The term "exemplary" used throughout this description means "serving as an example, instance, or illustration," and should not necessarily be construed as preferred or advantageous over other embodiments. The detailed description includes specific details for providing a thorough understanding of the presently disclosed method and system. However, it will be apparent to those skilled in the art that the presently disclosed process may be practiced without these specific details. In some instances, well-known structures and devices are shown in block diagram form in order to avoid obscuring the concepts of the presently disclosed method and system.

In the present specification, an embodiment showing a singular component should not be considered limiting. Rather, the subject matter preferably encompasses other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present subject matter encompasses present and future known equivalents to the known components referred to herein by way of illustration.

Transparent display screen on mobile device for color, shade and coating defect identification. On a single layer or holograph only screen, or on multiple transparent display layer screen; while viewing through the transparent display layer, use part of transparent displayer as shade guide in translucent form, for translucent colors such as color of liquid seen through a glass, and gas color may be compared.

Viewing directly through part of transparent display screen for color comparison (color match seen edge to edge, since only part of transparent display screen is used as color comparison chart), to overcome total image viewed through camera view played on non-transparent display screen to overcome RGB (red, green and blue lights) limitations, which applies to camera view displayed on type of non-transparent screen on mobile device.

On a multiple layered transparent display screen, utilizing top layer to display defects as parallax image, another layer showing colors and for non-translucent colors, also utilizing last layer or image support in form of non-transparency/opaque layer for the color sample. Together to show type of defect associated with color coating system and color.

The present disclosure relates to mobile electronic device with a transparent display screen. Electronic mobile devices are improving display screens and technical capabilities. With SoC (system on chip) making hardware in nanometer critical dimensions size and being reduced smaller. Hardware miniaturized to be concealed behind small areas making it possible to incorporate transparent screens for electronic mobile device. However, with transparent display screens, there are more functions that need to be addressed and provided as herein disclosed. Such as comparison, use of transparent screen while it is not being view by the user while the electronic mobile device is next to device owner's ear or held in front of the user.

The application relates to electronic mobile device with transparent display screens. Electronic mobile device with transparent display screens will include electronic components, which makes the device function. This Application is intended to enhance and explore usage of transparent display screens for comparison for color, shades of liquid/gas and coating defects. This application is not intended to replace Spectrophotometer, but to serve as better reference to determine color, shades of translucent colors, and texture defects which is not in 2D form. Mobile device with multiple transparent display layers to be utilize transparent display layer or layers to show coating defects in parallax image over base color layer (parallax image may be shown on top and or bottom of color layer per type of coating defect).

FIG. 1 provides a view of mobile device with transparent display screen with color/shade sample being used to compared and viewed through transparent display screen instead of camera view displayed on to type of LCD/LED screen. FIG. 1, thus, provides a view of an image as seen through a transparent display screen of a mobile electronic device for demonstrating aspects of the present disclosure. Referring to FIG. 1, transparent display screen 10 is placed in front of beverage 12, for example. Beverage 12 includes glass 14 and liquid 16. Liquid 16, as seen through transparent display screen 10 may have a property of translucence do as to capture ambient light. In order to properly measure translucence, texture, light variations and other image qualities, the present disclosure uses a shade/color sample 18 to compare and match with the perceived color, texture, and translucence, and other properties of liquid 16. By providing a variety of color, shading and texture controls, the present disclosure makes possible a much more accurate assessment of the color of liquid 16, for example.

Figure 2:
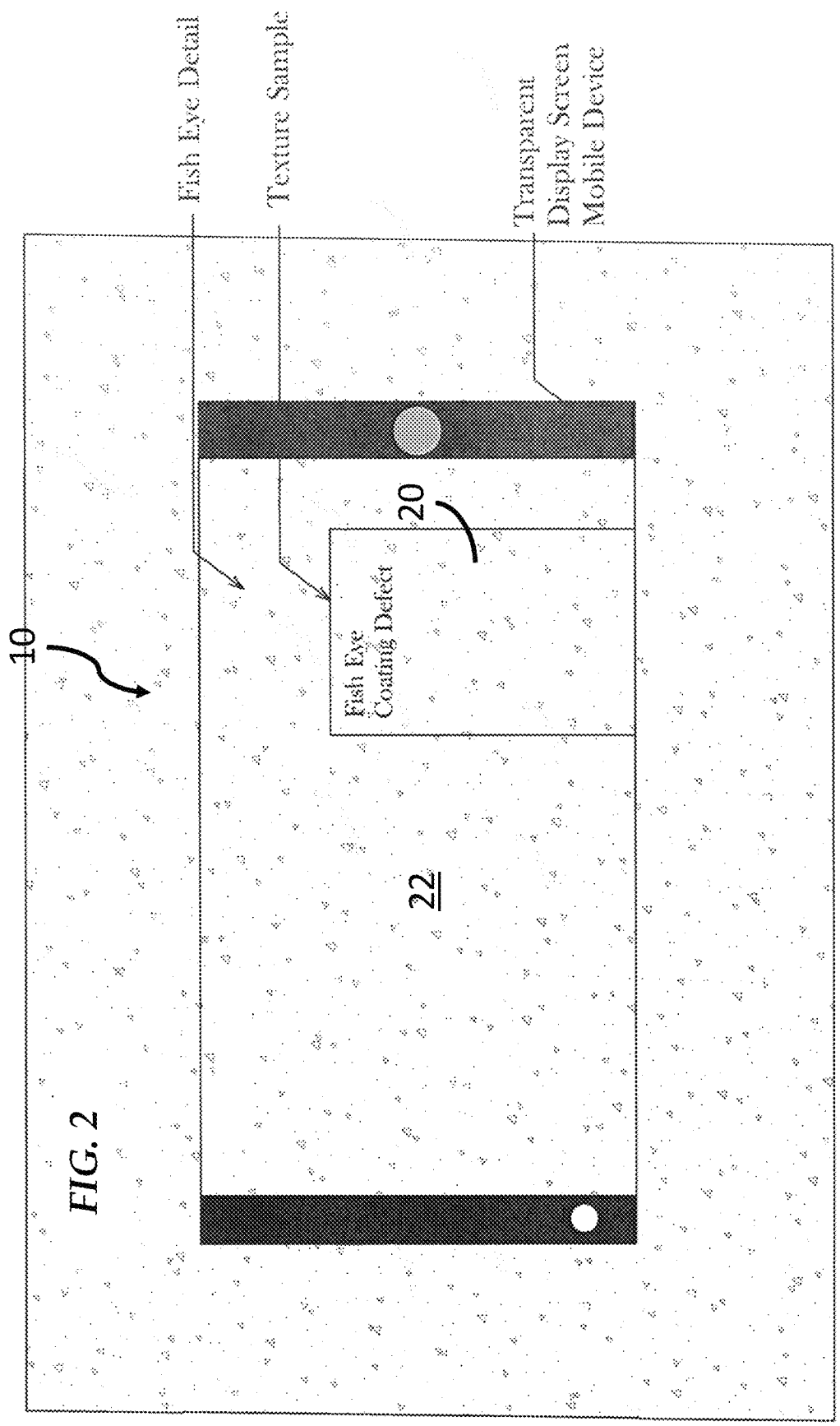
FIG. 2 is a view of an image as seen through a transparent display screen of a mobile electronic device for displaying texture and shading aspects of the present disclosure.

FIG. 2 is a view of an image as seen through a transparent display screen 10 of a mobile electronic device for displaying texture and shading aspects of the present disclosure.

Thus, in FIG. 2, transparent display screen 10 is placed in front of a texture sample 20 that may include a fish eye coating defect. In order to accurately assess the influence of the fish eye coating defect, the present disclosure includes the ability to create a fish eye texture 22 on transparent display screen 10. Matching the fish eye texture 22 on transparent display screen 10 with the fish eye texture on texture sample 20 provides digital and reproducible optical data that may be useful for accurately assessing the influence of the fish eye texture in texture sample 20.

Figure 3:
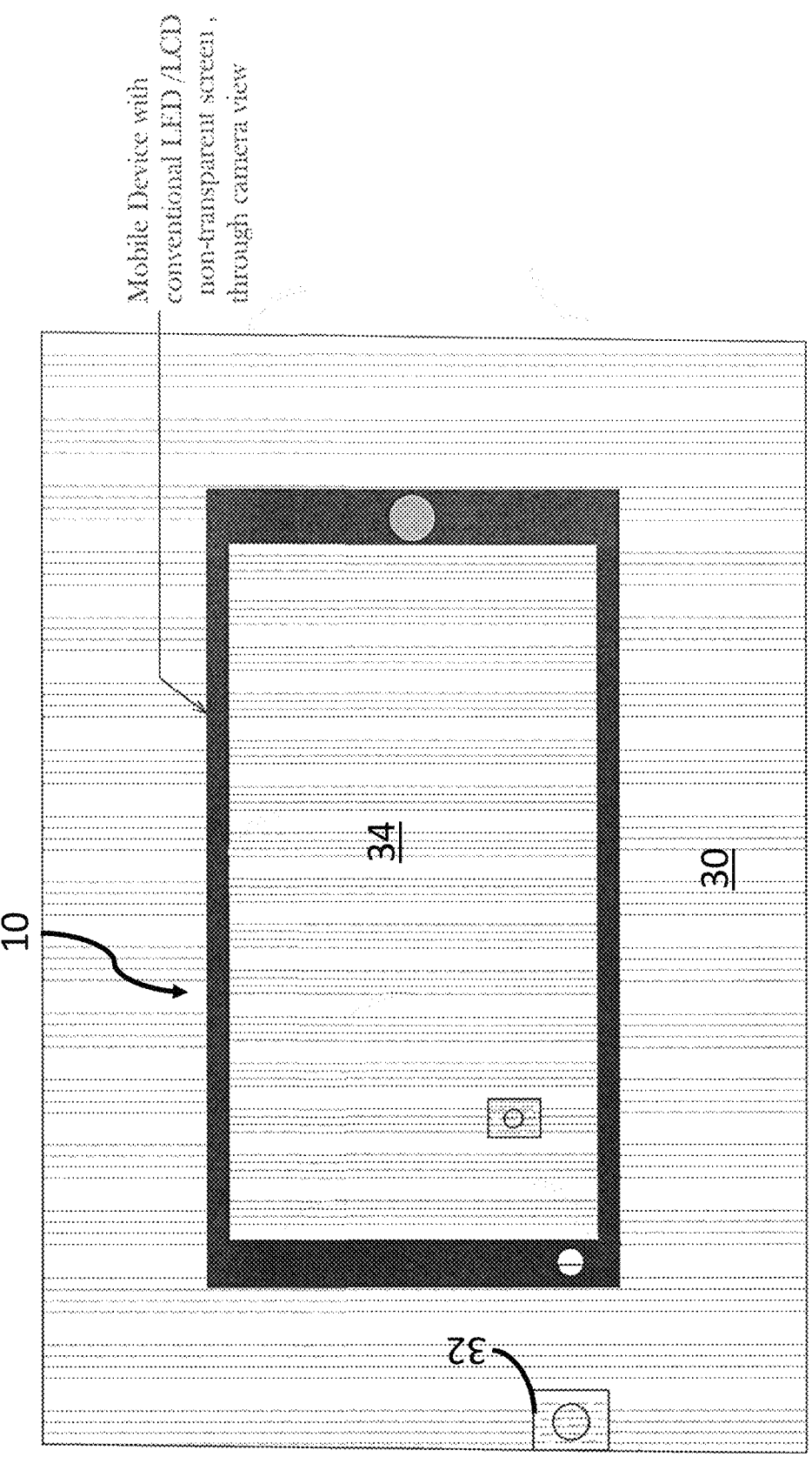
FIG. 3 is a view of an image as seen through a transparent display screen of a mobile electronic device for demonstrating dimensional, depth, and other aspects of the present disclosure.

FIG. 3 is a view of an image as seen through a transparent display screen 10 of a mobile electronic device for demonstrating dimensional, depth, and other aspects of the present disclosure. Thus, on transparent display screen 10 appears wall 30 on which appears control switch 32. Wallpaper 34, as seen through transparent display screen 10. Note that the image of wall 30, as seen through transparent display screen 10 is smaller in dimension, which may distort perception of texture, shading, and other aspects of the transparent display screen 10. According to the teachings of the present disclosure, here is provided the ability to appreciate and generate optical data respecting these variations.

An important aspect of the present disclosure includes three-dimensional touch control. The ability to push or vary pressure on the three-dimensional screen and the rate at which the pressure is applied would provide the ability to control the three-dimensional perception that would be recorded or used on the electronic device display screen. In addition, there is the ability to adjust the color that is perceived by the electronic device according to the controls of the user in the perception of the color in or through the electronic display screen transparent display.

The system uses at least one transparent display screen comprises a single display screen having at least one bonded monolithic form or a layered monolithic form. The system further includes optical processing data and optical processing instructions and algorithms for storing in the memory associated with the electronic mobile device and executing on the computer processor associated with the electronic mobile device for controllably varying the translucence of said at least one transparent display screen through a translucence range of zero translucence or opaque to 100% translucence or transparent. The system further includes optical processing data and optical processing instructions and algorithms for storing in the memory associated with the electronic mobile device and executing on the computer processor associated with the electronic mobile device for generating suggestions to a user for determining possible factors causing a color value for said first perceived color of interest to differ from a color value for said second perceived color of interest.

Another aspect of the present disclosure includes color shade and texture matching including three-dimensional and parallax touchscreen operation which can distinguish pressure differences in touch screen control. Using pressure differences, the perception of texture and depth can be significantly enhanced for uses of the present disclosure.

A further aspect of the present disclosure includes the ability to provide to a user options in matching color and texture for various objects with use of different levels of pressure applied to the transparent touch screen of a mobile electronic device. For example, a user can choose texture, but color has to be changed or vice versa, with different level of pressure, user can leave texture as is and just change the color. These control variations make the user experience much richer and rewarding, because of the ability to respond to varying levels of pressure on to touch screen.

The present disclosure includes the aspect of the ability to appreciate how objects with same color and different textures may have different perceived color parameters. For example, in considering paint as it dries, color might match but there could be at least 20 different textures it could appear with it. With paint drying or with defects like cracking, fish eye looking defects, peeling and etc., the color matching and analysis system of the present disclosure gives the ability to address such variations.

The present disclosure further includes the ability to use a parallax image to provide the ability to make more valuable distinctions between colors as a function of the texture of the particular object. By incorporating the concept of having dual transparent screens associated with a single mobile electronic device, the present disclosure provides the ability to determine various aspects of parallax images to control the way images are collected and may be responded to using multiple transparent screens.

The present disclosure further provides the ability to address texture differences in a three-dimensional screen for a variety of applications, including construction, painting, texture with foods, other aspects of perception where the ability to perceive an image through the transparent screen at the same time associate with the particular textures and other dimensional aspect of the object. This aspect provides the ability through the transparent display screen of perceiving objects characteristics that otherwise it cannot be perceived.

Figure 4A:
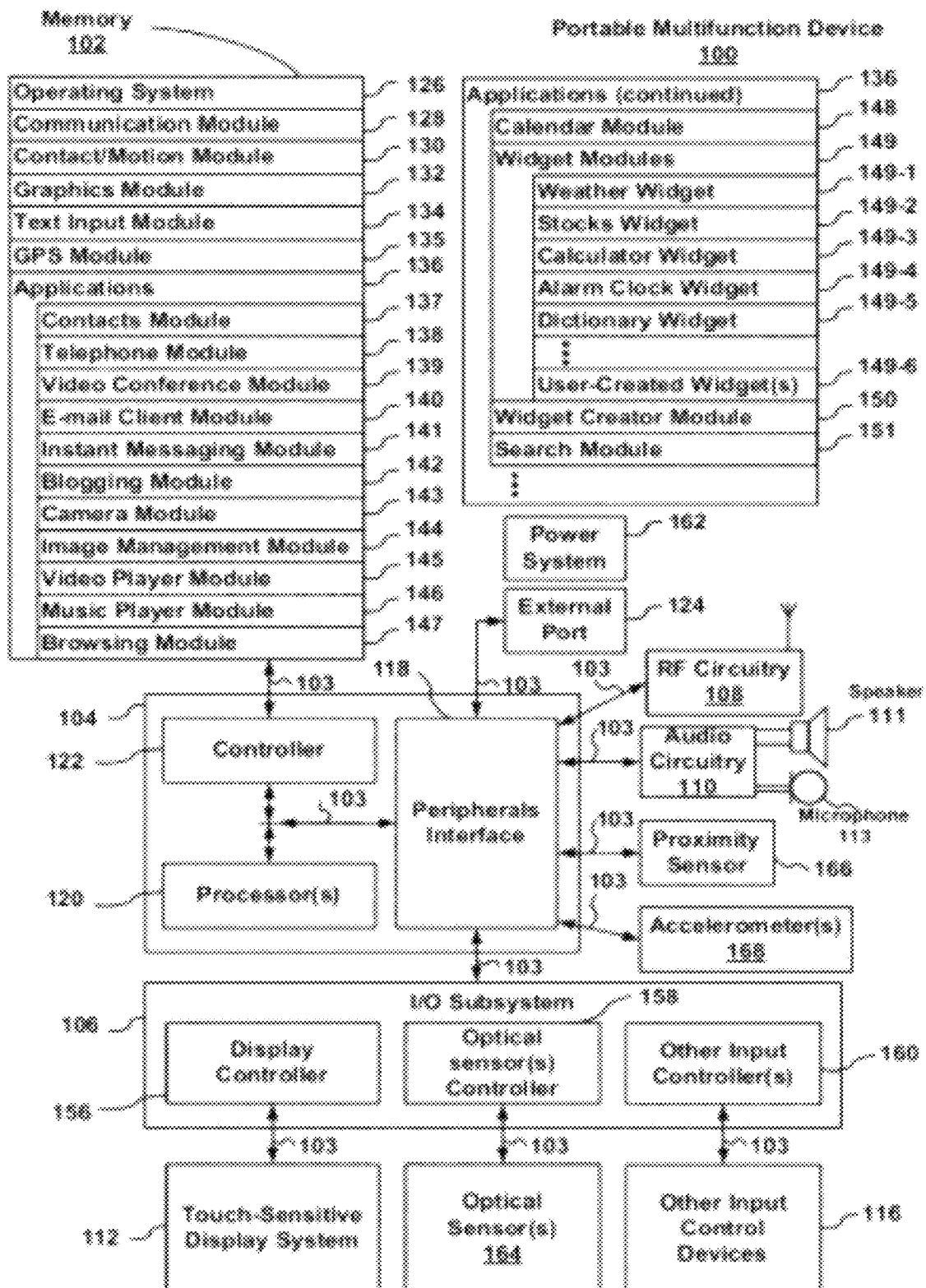
FIGS. 4A and 4B are block diagrams illustrating portable multifunction devices with touch-sensitive displays in accordance with some embodiments.
Figure 4B:
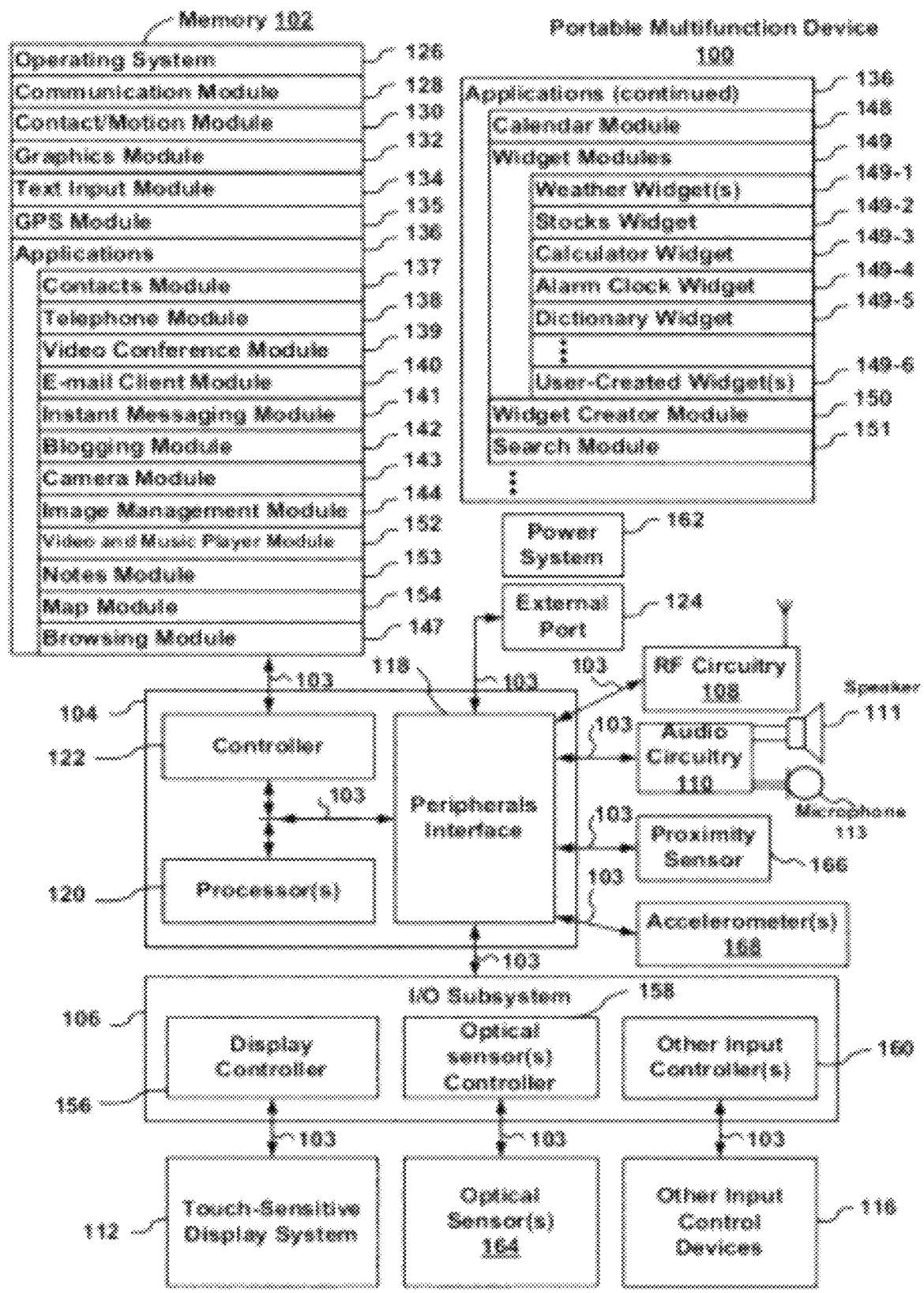

FIGS. 4A and 4B are block diagrams illustrating portable multifunction devices 100 with touch-sensitive displays 112 in accordance with some embodiments for the presently disclosed method, system, and integrated medical imaging system for forming a correlated view of human or other animal anatomy with electromagnetic spectrum images with non-optical electromagnetic images of human or other animal anatomy. The touch-sensitive display 112 is sometimes called a "touch screen" for convenience and may also be known as or called a touch-sensitive display system. The device 100 may include a memory 102 (which may include one or more computer readable storage mediums), a memory controller 122, one or more processing units (CPU's) 120, a peripherals interface 118, RF circuitry 108, audio circuitry 110, a speaker 111, a microphone 113, an input/output (I/O) subsystem 106, other input or control devices 116, and an external port 124. The device 100 may include one or more optical sensors 164. These components may communicate over one or more communication buses or signal lines 103.

It should be appreciated that the device 100 is only one example of a portable multifunction device 100, and that the device 100 may have more or fewer components than shown, may combine two or more components, or a may have a different configuration or arrangement of the components. The various components shown in FIGS. 4A and 4B may be implemented in hardware, software or a combination of both hardware and software, including one or more signal processing and/or application specific integrated circuits.

Memory 102 may include high-speed random-access memory and may also include non-volatile memory, such as one or more magnetic disk storage devices, flash memory devices, or other non-volatile solid-state memory devices. Access to memory 102 by other components of the device 100, such as the CPU 120 and the peripherals interface 118, may be controlled by the memory controller 122.

The peripherals interface 118 couples the input and output peripherals of the device to the CPU 120 and memory 102. The one or more processors 120 run or execute various software programs and/or sets of instructions stored in memory 102 to perform various functions for the device 100 and to process data.

In some embodiments, the peripherals interface 118, the CPU 120, and the memory controller 122 may be implemented on a single chip, such as a chip 104. In some other embodiments, they may be implemented on separate chips.

The RF (radio frequency) circuitry 108 receives and sends RF signals, also called electromagnetic signals. The RF circuitry 108 converts electrical signals to/from electromagnetic signals and communicates with communications networks and other communications devices via the electromagnetic signals. The RF circuitry 108 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

The RF circuitry 108 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry 110, the speaker 111, and the microphone 113 provide an audio interface between a user and the device 100. The audio circuitry 110 receives audio data from the peripherals interface 118, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to the peripherals interface 118 for processing. Audio data may be retrieved from and/or transmitted to memory 102 and/or the RF circuitry 108 by the peripherals interface 118. In some embodiments, the audio circuitry 110 also includes a headset jack (e.g. 212, FIG. 2). The headset jack provides an interface between the audio circuitry 110 and removable audio input/output peripherals, such as output-only headphones or a headset with both output (e.g., a headphone for one or both ears) and input (e.g., a microphone).

The I/O subsystem 106 couples input/output peripherals on the device 100, such as the touch screen 112 and other input/control devices 116, to the peripherals interface 118. The I/O subsystem 106 may include a display controller 156 and one or more input controllers 160 for other input or control devices. The one or more input controllers 160 receive/send electrical signals from/to other input or control devices 116. The other input/control devices 116 may include physical buttons (e.g., push buttons, rocker buttons, etc.), dials, slider switches, joysticks, click wheels, and so forth. In some alternate embodiments, input controller(s) 160 may be coupled to any (or none) of the following: a keyboard, infrared port, USB port, and a pointer device such as a mouse. The one or more buttons (e.g., 208, FIG. 5) may include an up/down button for volume control of the speaker 111 and/or the microphone 113. The one or more buttons may include a push button (e.g., 206, FIG. 2). A quick press of the push button may disengage a lock of the touch screen 112 or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button (e.g., 206) may turn power to the device 100 on or off. The user may be able to customize a functionality of one or more of the buttons. The touch screen 112 is used to implement virtual or soft buttons and one or more soft keyboards.

The touch-sensitive touch screen 112 provides an input interface and an output interface between the device and a user. The display controller 156 receives and/or sends electrical signals from/to the touch screen 112. The touch screen 112 displays visual output to the user. The visual output may include graphics, text, icons, video, and any combination thereof (collectively termed "graphics"). In some embodiments, some or all of the visual output may correspond to user-interface objects, further details of which are described below.

A touch screen 112 has a touch-sensitive surface, sensor or set of sensors that accepts input from the user based on haptic and/or tactile contact. The touch screen 112 and the display controller 156 (along with any associated modules and/or sets of instructions in memory 102) detect contact (and any movement or breaking of the contact) on the touch screen 112 and converts the detected contact into interaction with user-interface objects (e.g., one or more soft keys, icons, web pages or images) that are displayed on the touch screen. In an exemplary embodiment, a point of contact between a touch screen 112 and the user corresponds to a finger of the user.

The touch screen 112 may use LCD (liquid crystal display) technology, or LPD (light emitting polymer display) technology, although other display technologies may be used in other embodiments. The touch screen 112 and the display controller 156 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 112.

A touch-sensitive display in some embodiments of the touch screen 112 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in their entirety. However, a touch screen 112 displays visual output from the portable device 100, whereas touch sensitive tablets do not provide visual output.

A touch-sensitive display in some embodiments of the touch screen 112 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 112 may have a resolution in excess of 100 dpi. In an exemplary embodiment, the touch screen has a resolution of approximately 160 dpi. The user may make contact with the touch screen 112 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, the device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 112 or an extension of the touch-sensitive surface formed by the touch screen.

The device 100 also includes a power system 162 for powering the various components. The power system 162 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The device 100 may also include one or more optical sensors 164. FIGS. 4A and 4B show an optical sensor coupled to an optical sensor controller 158 in I/O subsystem 106. The optical sensor 164 may include charge-coupled device (CCD) or complementary metal-oxide semiconductor (CMOS) phototransistors. The optical sensor 164 receives light from the environment, projected through one or more lens, and converts the light to data representing an image. In conjunction with an imaging module 143 (also called a camera module), the optical sensor 164 may capture still images or video. In some embodiments, an optical sensor is located on the back of the device 100, opposite the touch screen display 112 on the front of the device, so that the touch screen display may be used as a viewfinder for either still and/or video image acquisition.

In some embodiments, an optical sensor is located on the front of the device so that the user's image may be obtained for videoconferencing while the user views the other video conference participants on the touch screen display. In some embodiments, the position of the optical sensor 164 can be changed by the user (e.g., by rotating the lens and the sensor in the device housing) so that a single optical sensor 164 may be used along with the touch screen display for both video conferencing and still and/or video image acquisition.

The device 100 may also include one or more proximity sensors 166. FIGS. 4A and 4B show a proximity sensor 166 coupled to the peripherals interface 118. Alternately, the proximity sensor 166 may be coupled to an input controller 160 in the I/O subsystem 106. The proximity sensor 166 may perform as described in U.S. patent application Ser. No. 11/241,839, "Proximity Detector In Handheld Device," filed Sep. 30, 2005; U.S. patent application Ser. No. 11/240,788, "Proximity Detector In Handheld Device," filed Sep. 30, 2005; U.S. patent application Ser. No. 11/620,702, "Using Ambient Light Sensor To Augment Proximity Sensor Output"; U.S. patent application Ser. No. 11/586,862, "Automated Response To And Sensing Of User Activity In Portable Devices," filed Oct. 24, 2006; and U.S. patent application Ser. No. 11/638,251, "Methods And Systems For Automatic Configuration Of Peripherals," which are hereby incorporated by reference in their entirety. In some embodiments, the proximity sensor turns off and disables the touch screen 112 when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

The device 100 may also include one or more accelerometers 168. FIGS. 4A and 4B show an accelerometer 168 coupled to the peripherals interface 118. Alternately, the accelerometer 168 may be coupled to an input controller 160 in the I/O subsystem 106. The accelerometer 168 may perform as described in U.S. Patent Publication No. 20050190059, "Acceleration-based Theft Detection System for Portable Electronic Devices," and U.S. Patent Publication No. 20060017692, "Methods and Apparatuses for Operating A Portable Device Based on An Accelerometer," both of which are which are incorporated by reference in their entirety. In some embodiments, information is displayed on the touch screen display in a portrait view or a landscape view based on an analysis of data received from the one or more accelerometers.

In some embodiments, the software components stored in memory 102 may include an operating system 126, a communication module (or set of instructions) 128, a contact/motion module (or set of instructions) 130, a graphics module (or set of instructions) 132, a text input module (or set of instructions) 134, a Global Positioning System (GPS) module (or set of instructions) 135, and applications (or set of instructions) 136.

The operating system 126 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 128 facilitates communication with other devices over one or more external ports 124 and also includes various software components for handling data received by the RF circuitry 108 and/or the external port 124. The external port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) devices.

The contact/motion module 130 may detect contact with the touch screen 112 (in conjunction with the display controller 156) and other touch sensitive devices (e.g., a touchpad or physical click wheel). The contact/motion module 130 includes various software components for performing various operations related to detection of contact, such as determining if contact has occurred, determining if there is movement of the contact and tracking the movement across the touch screen 112, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module 130 and the display controller 156 also detects contact on a touchpad. In some embodiments, the contact/motion module 130 and the controller 160 detects contact on a click wheel.

The graphics module 132 includes various known software components for rendering and displaying graphics on the touch screen 112, including components for changing the intensity of graphics that are displayed. As used herein, the term "graphics" includes any object that can be displayed to a user, including without limitation text, web pages, icons (such as user-interface objects including soft keys), digital images, videos, animations and the like. An animation in this context is a display of a sequence of images that gives the appearance of movement and informs the user of an action that has been performed (such as moving an email message to a folder). In this context, a respective animation that confirms an action by the user of the device typically takes a predefined, finite amount of time, such as an amount of time between 0.2 and 1.0 seconds, or between 0.5 and 2.0 seconds, depending on the context.

The text input module 134, which may be a component of graphics module 132, provides soft keyboards for entering text in various applications (e.g., contacts 137, e-mail 140, IM 141, blogging 142, browser 147, and any other application that needs text input).

The GPS module 135 determines the location of the device and provides this information for use in various applications (e.g., to telephone 138 for use in location-based dialing, to camera 143 and/or blogger 142 as picture/video metadata, and to applications that provide location-based services such as weather widgets, local yellow page widgets, and map/navigation widgets).

The applications 136 may include the following modules (or sets of instructions), or a subset or superset thereof:
  a contacts module 137 (sometimes called an address book or contact list);
  a telephone module 138;
  a video conferencing module 139;
  an e-mail client module 140;
  an instant messaging (IM) module 141;
  a blogging module 142;
  a camera module 143 for still and/or video images;
  an image management module 144;
  a video player module 145;
  a music player module 146;
  a browser module 147;
  a calendar module 148;
  widget modules 149, which may include weather widget 149-1, stocks widget 149-2, calculator widget 149-3, alarm clock widget 149-4, dictionary widget 149-5, and other widgets obtained by the user, as well as user-created widgets 149-6;
  widget creator module 150 for making user-created widgets 149-6;
  search module 151;
  video and music player module 152, which merges video player module 145 and music player module 146;
  notes module 153; and/or
  map module 154.

Examples of other applications 136 that may be stored in memory 102 include other word processing applications, JAVA-enabled applications, encryption, digital rights management, voice recognition, and voice replication.

In conjunction with touch screen 112, display controller 156, contact module 130, graphics module 132, and text input module 134, the contacts module 137 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference 139, e-mail 140, or IM 141; and so forth. Embodiments of user interfaces and associated processes using contacts module 137 are described further below.

In conjunction with RF circuitry 108, audio circuitry 110, speaker 111, microphone 113, touch screen 112, display controller 156, contact module 130, graphics module 132, and text input module 134, the telephone module 138 may be used to enter a sequence of characters corresponding to a telephone number, access one or more telephone numbers in the address book 137, modify a telephone number that has been entered, dial a respective telephone number, conduct a conversation and disconnect or hang up when the conversation is completed. As noted above, the wireless communication may use any of a plurality of communications standards, protocols and technologies. Embodiments of user interfaces and associated processes using telephone module 138 are described further below.

In conjunction with RF circuitry 108, audio circuitry 110, speaker 111, microphone 113, touch screen 112, display controller 156, optical sensor 164, optical sensor controller 158, contact module 130, graphics module 132, text input module 134, contact list 137, and telephone module 138, the videoconferencing module 139 may be used to initiate, conduct, and terminate a video conference between a user and one or more other participants.

In conjunction with RF circuitry 108, touch screen 112, display controller 156, contact module 130, graphics module 132, and text input module 134, the e-mail client module 140 may be used to create, send, receive, and manage e-mail. In conjunction with image management module 144, the e-mail module 140 makes it very easy to create and send e-mails with still or video images taken with camera module 143. Embodiments of user interfaces and associated processes using e-mail module 140 are described further below.

In conjunction with RF circuitry 108, touch screen 112, display controller 156, contact module 130, graphics module 132, and text input module 134, the instant messaging module 141 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS). Embodiments of user interfaces and associated processes using instant messaging module 141 are described further below.

In conjunction with RF circuitry 108, touch screen 112, display controller 156, contact module 130, graphics module 132, text input module 134, image management module 144, and browsing module 147, the blogging module 142 may be used to send text, still images, video, and/or other graphics to a blog (e.g., the user's blog).

In conjunction with touch screen 112, display controller 156, optical sensor(s) 164, optical sensor controller 158, contact module 130, graphics module 132, and image management module 144, the camera module 143 may be used to capture still images or video (including a video stream) and store them into memory 102, modify characteristics of a still image or video, or delete a still image or video from memory 102. Embodiments of user interfaces and associated processes using camera module 143 are described further below.

In conjunction with touch screen 112, display controller 156, contact module 130, graphics module 132, text input module 134, and camera module 143, the image management module 144 may be used to arrange, modify or otherwise manipulate, label, delete, present (e.g., in a digital slide show or album), and store still and/or video images. Embodiments of user interfaces and associated processes using image management module 144 are described further below.

In conjunction with touch screen 112, display controller 156, contact module 130, graphics module 132, audio circuitry 110, and speaker 111, the video player module 145 may be used to display, present or otherwise play back videos (e.g., on the touch screen or on an external, connected display via external port 124). Embodiments of user interfaces and associated processes using video player module 145 are described further below.

In conjunction with touch screen 112, display system controller 156, contact module 130, graphics module 132, audio circuitry 110, speaker 111, RF circuitry 108, and browser module 147, the music player module 146 allows the user to download and play back recorded music and other sound files stored in one or more file formats, such as MP3 or AAC files. In some embodiments, the device 100 may include the functionality of an MP3 player, such as an iPod (trademark of Apple Computer, Inc.). Embodiments of user interfaces and associated processes using music player module 146 are described further below.

In conjunction with RF circuitry 108, touch screen 112, display system controller 156, contact module 130, graphics module 132, and text input module 134, the browser module 147 may be used to browse the Internet, including searching, linking to, receiving, and displaying web pages or portions thereof, as well as attachments and other files linked to web pages. Embodiments of user interfaces and associated processes using browser module 147 are described further below.

In conjunction with RF circuitry 108, touch screen 112, display system controller 156, contact module 130, graphics module 132, text input module 134, e-mail module 140, and browser module 147, the calendar module 148 may be used to create, display, modify, and store calendars and data associated with calendars (e.g., calendar entries, to do lists, etc.). Embodiments of user interfaces and associated processes using calendar module 148 are described further below.

In conjunction with RF circuitry 108, touch screen 112, display system controller 156, contact module 130, graphics module 132, text input module 134, and browser module 147, the widget modules 149 are mini-applications that may be downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display system controller 156, contact module 130, graphics module 132, text input module 134, and browser module 147, the widget creator module 150 may be used by a user to create widgets (e.g., turning a user-specified portion of a web page into a widget).

In conjunction with touch screen 112, display system controller 156, contact module 130, graphics module 132, and text input module 134, the search module 151 may be used to search for text, music, sound, image, video, and/or other files in memory 102 that match one or more search criteria (e.g., one or more user-specified search terms).

In conjunction with touch screen 112, display controller 156, contact module 130, graphics module 132, and text input module 134, the notes module 153 may be used to create and manage notes, to do lists, and the like.

In conjunction with RF circuitry 108, touch screen 112, display system controller 156, contact module 130, graphics module 132, text input module 134, GPS module 135, and browser module 147, the map module 154 may be used to receive, display, modify, and store maps and data associated with maps (e.g., driving directions; data on stores and other points of interest at or near a particular location; and other location-based data).

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module 145 may be combined with music player module 146 into a single module (e.g., video and music player module 152, FIG. 4B). In some embodiments, memory 102 may store a subset of the modules and data structures identified above. Furthermore, memory 102 may store additional modules and data structures not described above.

In some embodiments, the device 100 is a device where operation of a predefined set of functions on the device is performed exclusively through a touch screen 112 and/or a touchpad. By using a touch screen and/or a touchpad as the primary input/control device for operation of the device 100, the number of physical input/control devices (such as push buttons, dials, and the like) on the device 100 may be reduced.

The predefined set of functions that may be performed exclusively through a touch screen and/or a touchpad include navigation between user interfaces. In some embodiments, the touchpad, when touched by the user, navigates the device 100 to a main, home, or root menu from any user interface that may be displayed on the device 100. In such embodiments, the touchpad may be referred to as a "menu button." In some other embodiments, the menu button may be a physical push button or other physical input/control device instead of a touchpad.

Figure 5:
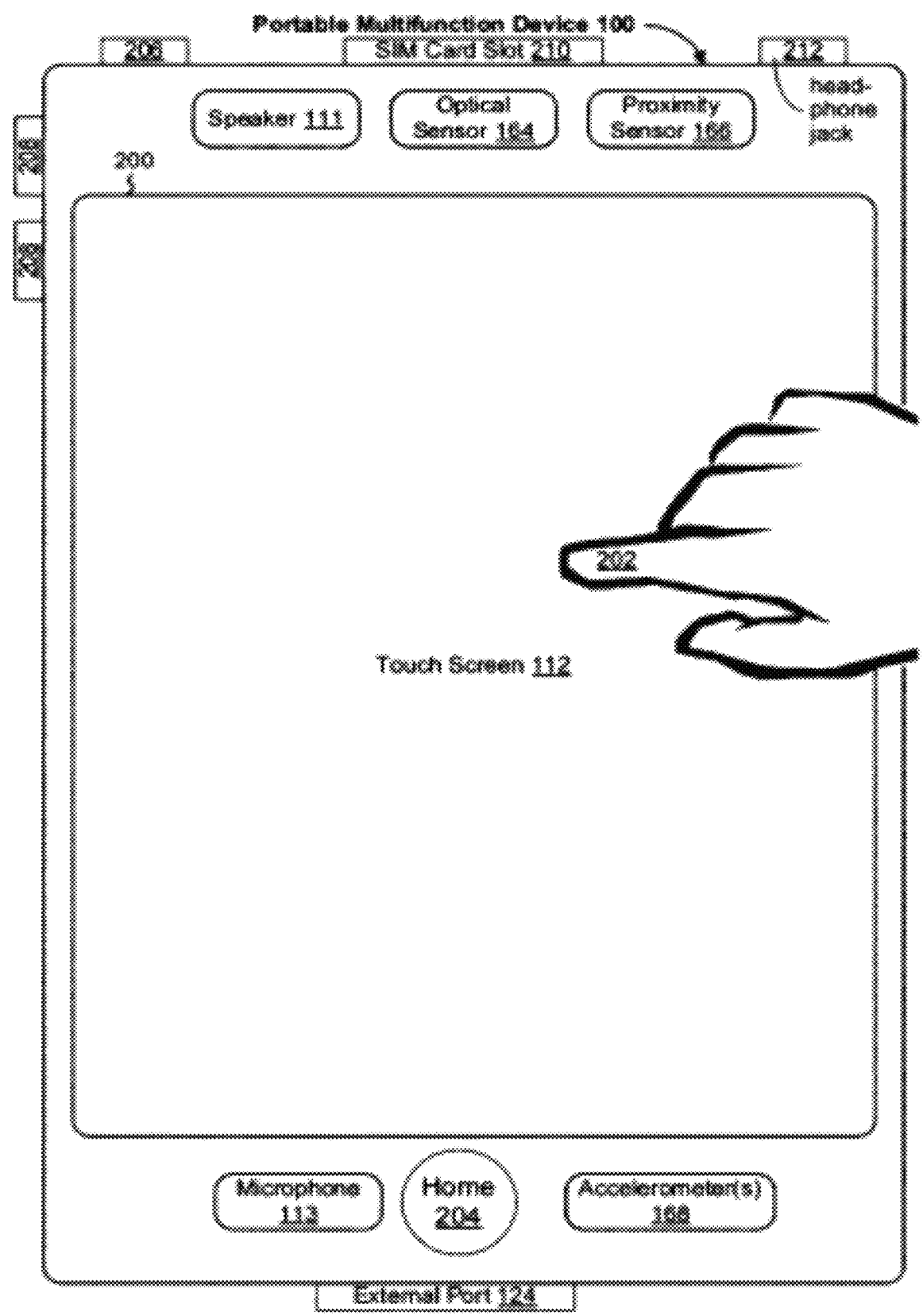
FIG. 5 illustrates a portable multifunction device having a touch screen in accordance with some embodiments.

FIG. 5 illustrates a portable multifunction device 100 having a touch screen 112 in accordance with some embodiments. The touch screen may display one or more graphics within user interface (UI) 200. In this embodiment, as well as others described below, a user may select one or more of the graphics by making contact or touching the graphics, for example, with one or more fingers 202 (not drawn to scale in the FIGURE). In some embodiments, selection of one or more graphics occurs when the user breaks contact with the one or more graphics. In some embodiments, the contact may include a gesture, such as one or more taps, one or more swipes (from left to right, right to left, upward and/or downward) and/or a rolling of a finger (from right to left, left to right, upward and/or downward) that has made contact with the device 100. In some embodiments, inadvertent contact with a graphic may not select the graphic. For example, a swipe gesture that sweeps over an application icon may not select the corresponding application when the gesture corresponding to selection is a tap.

The device 100 may also include one or more physical buttons, such as "home" or menu button 204. As described previously, the menu button 204 may be used to navigate to any application 136 in a set of applications that may be executed on the device 100. Alternatively, in some embodiments, the menu button is implemented as a soft key in a GUI in touch screen 112.

In one embodiment, the device 100 includes a touch screen 112, a menu button 204, a push button 206 for powering the device on/off and locking the device, volume adjustment button(s) 208, a Subscriber Identity Module (SIM) card slot 210, a head set jack 212, and a docking/charging external port 124. The push button 206 may be used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, the device 100 also may accept verbal input for activation or deactivation of some functions through the microphone 113.

U.S. Pat. No. 9,367,093 to Pance, issued on Jun. 14, 2016 describes and claims a "Transparent Electronic Device for displaying images on a transparent display of an electronic device. The display may include one or more display screens as well as a flexible circuit for connecting the display screens with internal circuitry of the electronic device. Furthermore, the display screens may allow for overlaying of images over real-world viewable objects, as well as a visible window to be present on an otherwise opaque display screen. Additionally, the display may include active and passive display screens that may be utilized based on images to be displayed. The disclosure of U.S. Pat. No. 9,367,093 is expressly incorporated by reference, as contained fully herein.

Additional embodiments of the present disclosure made advantageous use of (a) light coding technology, (b) three-dimensional sensing using speckle patterns, (c) depth-varying light fields for three dimensional sensing, (d) systems and methods for imaging and image processing for creating an image having blurred and non-blurred areas, (e) real-time camera tracking using depth maps, and (f) depth map calculation in a stereo camera system, all as may be applicable to the present disclosure and the advantages thereof.

Light Coding Technology-PrimeSense' depth acquisition was enabled by "light coding" technology. Internet address http://www.i3du.gr/pdf/primesense.pdf provides a disclosure of the operation of light coding technology and here is expressly incorporated by reference in its entirety. The process may code a scene as here presented with near-IR light; light that returns distorted depending upon where things are. The solution then used a standard off-the-shelf CMOS image sensor to read the coded light back from the scene using various algorithms to triangulate and extract the 3D data. The product analyzed scenery in 3 dimensions with software, so that devices could interact with users.

U.S. Pat. No. 8,390,821B2 discloses and claims "Three-dimensional sensing using speckle patterns" for mapping of three-dimensional (3D) objects, and specifically to 3D optical imaging using speckle patterns, and is here expressly incorporated by reference in its entirety. This patent disclosure provides apparatus for 3D mapping of an object includes an illumination assembly, including a coherent light source and a diffuser, which are arranged to project a primary speckle pattern on the object. A single image capture assembly is arranged to capture images of the primary speckle pattern on the object from a single, fixed location and angle relative to the illumination assembly. A processor is coupled to process the images of the primary speckle pattern captured at the single, fixed angle so as to derive a 3D map of the object.

U.S. Patent Application Publication No. 20080106746 discloses a "Depth-varying light fields for three-dimensional sensing" for mapping three-dimensional (3D) objects, and specifically to 3D optical ranging and mapping, and is here expressly incorporated by reference in its entirety. The patent application publication shows a method for mapping includes projecting onto an object a pattern of multiple spots having respective positions and shapes, such that the positions of the spots in the pattern are uncorrelated, while the shapes share a common characteristic. An image of the spots on the object is captured and processed so as to derive a three-dimensional (3D) map of the object.

U.S. Patent Application Publication No. 20140192238 discloses a "System and Method for Imaging and Image Processing" for creating an image having blurred and non-blurred areas using an image capturing device and for creating an image with highlighted differences in an image sequence and is here expressly incorporated by reference in its entirety. The patent application publication shows for one or more objects of interest from a scene that are selected the calculation of depth information. Additionally, depth information of the scene is calculated. The calculated depth information of the one or more objects is compared with calculated depth information of the scene. Based on the comparison, a blur is applied to an image that includes the scene.

U.S. Pat. No. 9,242,171 discloses a "Real-time camera tracking using depth maps" for tracking the orientation and position of a camera as it moves in an environment and is here expressly incorporated by reference in its entirety. The patent shows a real-time camera tracking using depth maps. In an embodiment depth map frames are captured by a mobile depth camera at over 20 frames per second and used to dynamically update in real-time a set of registration parameters which specify how the mobile depth camera has moved. In examples the real-time camera tracking output is used for computer game applications and robotics. In an example, an iterative closest point process is used with projective data association and a point-to-plane error metric in order to compute the updated registration parameters. In an example, a graphics processing unit (GPU) implementation is used to optimize the error metric in real-time. In some embodiments, a dense 3D model of the mobile camera environment is used.

U.S. Patent Application Publication No. 20170069097 discloses a "Depth Map Calculation in a Stereo Camera System" for generating a depth map using a stereo camera system to capture two images of an object, determining a difference in blur between the two images at a particular point, and determining a depth for a depth map based on the difference in blur. US patent application publication No. 20170069097 is here expressly incorporated by reference in its entirety. The method includes obtaining a first image of a scene from a first image capture unit, the first image having a first depth-of-field (DOF), obtaining a second image of the scene from a second image capture unit, the second image having a second DOF that is different than the first DOF. Each pixel in the second image has a corresponding pixel in the first image. The method also includes generating a plurality of third images, each corresponding to a blurred version of the second image at the each of a plurality of specified depths, generating a plurality of fourth images, each representing a difference between the first image and one or the plurality of third images, and generating a depth map where each pixel in the depth map is based on the pixels in one of plurality of fourth images.

The present disclosure, using all of the subject herein presented and incorporated by reference, provides for the collection of information from a mobile device with transparent display screen, and mobile device with dual non-transparent screen facing front and rear (rear screen may be E-type reader) with utilization software, GPS/Location, date and time data and all sensors to include camera base 3D and or 3D sensor. Such functions and benefits include, and are not limited to (a) measuring the mobile device's distance from the advertisement viewers; (b) facial reaction as advertisement is being displayed; (c) eye position toward the advertisement while being displayed; (d) Body/clothing features to include size and mass of audience; (e) audience gender; (f) number of audience within sensor's area limits; (g) type of clothing audience are wearing; (h) surrounding environment information; (i) identify color; as well as (j) any other information sensors to include 3D sensor data may be able to collect with mobile device.

In conjunction with the data collection and functions as provided above, the disclosed subject matter discloses and expressly incorporates features and functions including a mobile software application to adjust, improve AR/MR images. These functions may include (a) refining an advertisement for a target audience; (b) enhancing advertisement for target audience; (c) adjusting the size of the advertisement or image; (d) enhancing the content of advertisement; (e) aligning the subject and generated image through transparent display screen; (f) changing the size of the generated advertisement, AR, MR image; (g) changing the duration of advertisement or image content; (h) adjusting the depth and angle of AR, MR image; (l) correcting the angle of view for parallax image; (j) aligning users viewing angle to display image AR, MR image color intensity to include translucent images; as well as (k) any other modifications to advertisement, as needed to increase improve visual and subject content.

With use of software and data collected such as GPS/location, time and date, on mobile device with transparent display screen, information/data collected from 3D sensor and or 3D camera sensor may include eyes, face position alignment toward the image and to the image being displayed on transparent display screen, object features to include size, surrounding environment, and any other information 3D sensor may be able to collect within mobile device's viewable area and or senor's area limit. With collected information, software apps may utilize to adjust depth, size, color, texture (shown in translucent parallax image), image intensity, angle of view of parallax images, translucency, subject content and any other information deemed important to application to improve Augmented Reality (AR), Mix Reality (MR) or Photo applications and for immediate or future application, while mobile device is in use with acknowledgement by device user.

In addition, with utilization front and rear 3D sensor on a mobile device, may be utilized align viewing angle of AR/MR (MR for blocking out unwanted objects) images with background viewed on transparent screen.

With improvement in sensor and software technology for mobile device, smart mobile devices can calculate color and texture (3D sensor) to match the pattern. For fine detail, device user may adjust or fine tune final selection. At present time, trained human eyes comparison cannot be matched for non-commercial applications. For matching or compare color or texture viewed through transparent display screen, texture may be shown in translucent for top layer and solid or translucent color as bottom layer of parallax image. For fluid or color in atmosphere space, color may be shown in translucent color.

Figure 6:
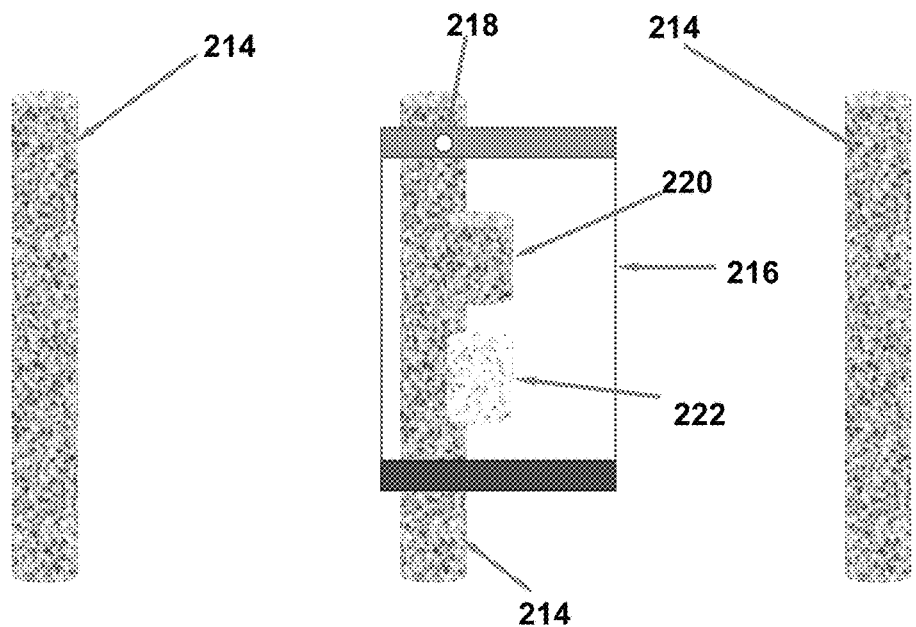
FIG. 6 shows an image of mobile device with transparent display screen being utilized for AR color sample and AR texture image sample comparison.

FIG. 6 shows an image of mobile device with transparent display screen 216 being utilized for AR color sample 220 and AR texture image sample 222 comparison of object 214 seen through transparent display screen. Built-in front 3D sensor 218 may be utilized to align viewing angle of AR and object being compared through transparent display screen.

Figure 7:
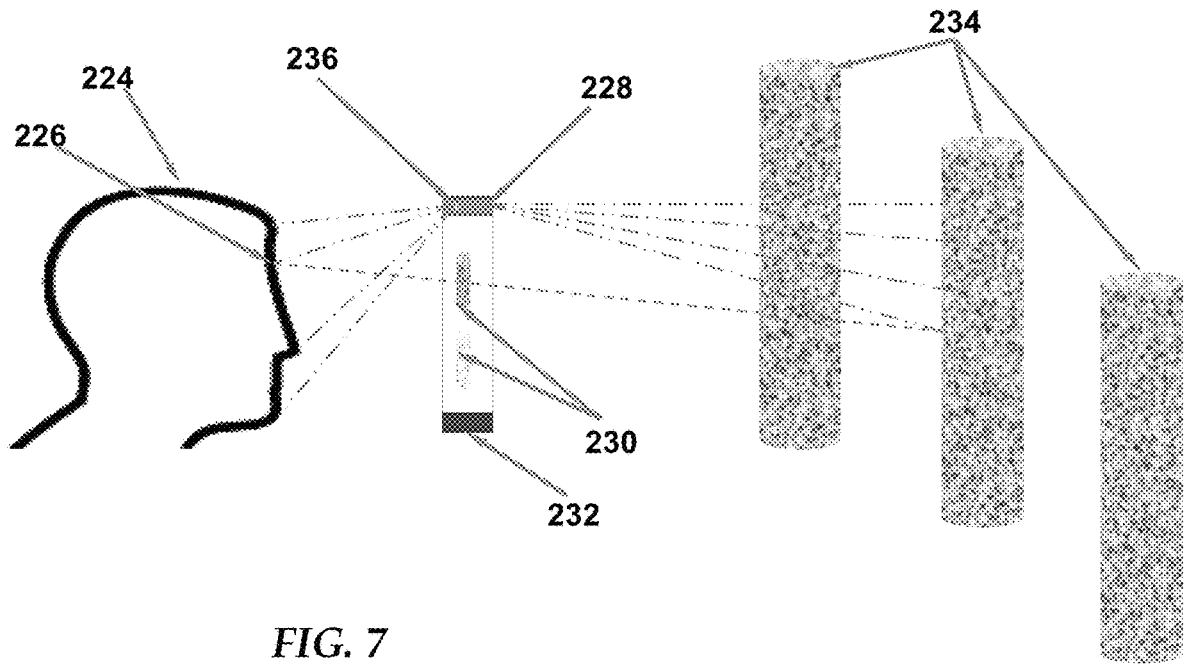
FIG. 7 presents an image of a device user viewing an object through mobile device transparent screen for comparing AR image, color and texture.

FIG. 7 presents an image of device user 224 viewing 226 an object 234 through mobile device transparent screen 232 for comparing AR image, color and texture 230. Front 3D sensor 236 focused on multiple points on user and rear 3D sensor 228 focused on multiple points of an object being to align AR image.

Figure 8:
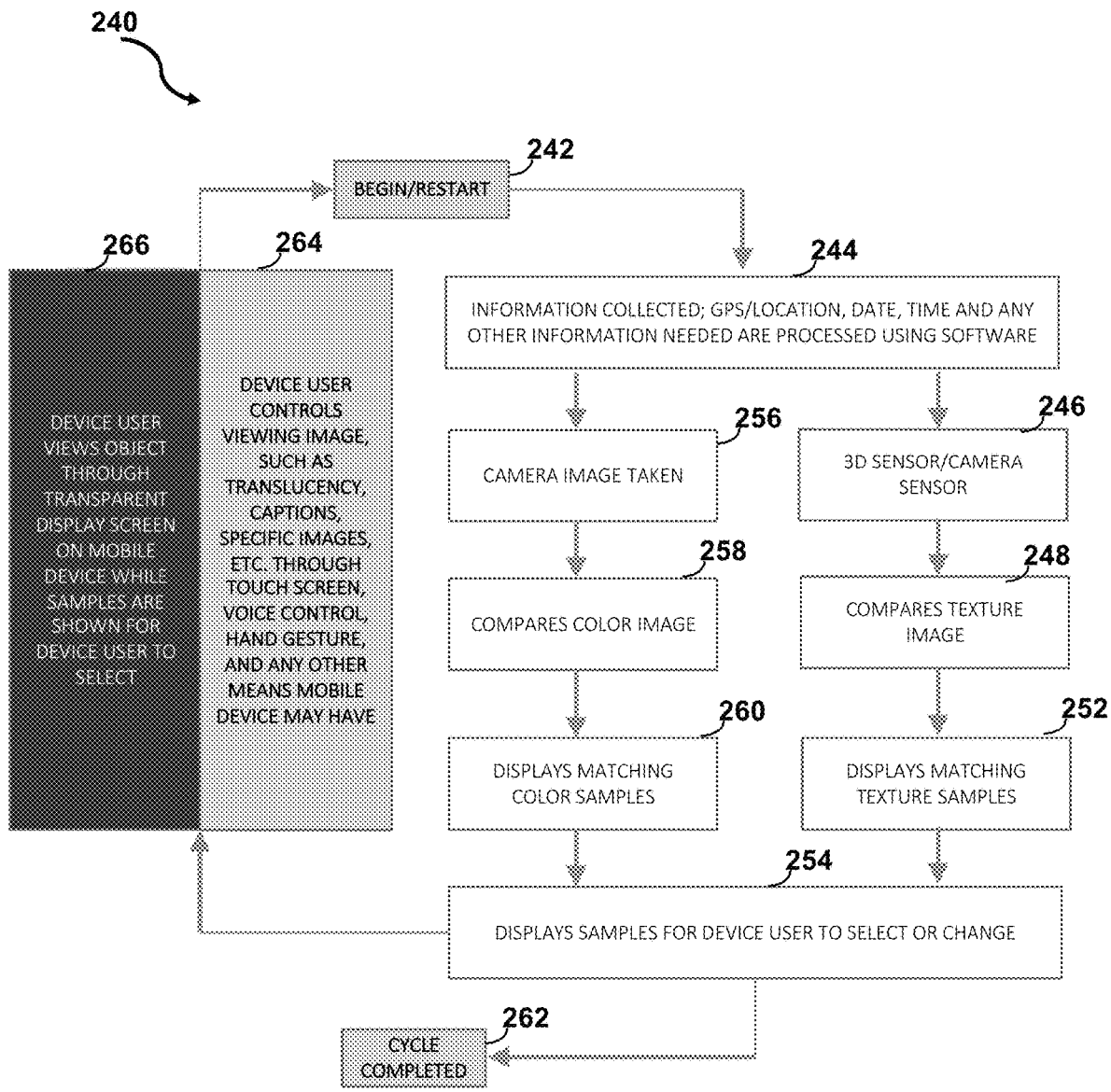
FIG. 8 presents a flow chart for an example using the teachings of the present disclosure.

FIG. 8 presents a flow chart 240 for an example beginning at step 242 and including the use of software, GPS/location, time and data, on mobile device with transparent display 244, information from 3D sensor 246, camera sensors 256 include texture 248 of object being compared to, color 258, and any other information needed. With collected information, sample of matching texture and color will be displayed for device user's final approval. Device user may manually choose matching 252 color 260 and texture 252. Then, the process displays samples for device user to select of change 254. The cycle may repeat and display through the transparent display 266 or permit the use of device user controls 264, for viewing image and other functions. At step 262, the process completes. This process can be modified or restructured as needed according to different operating systems and capabilities of different mobile devices.

Another aspect of the presently disclosed subject matter makes possible the use of a head mounted display system. One such head mounted display appears in U.S. Pat. No. 7,595,933, wherein a head mounted display system includes a remote laser light engine that generates laser light associated with a display signal. The full disclosure of U.S. Pat. No. 7,595,933 is herein expressly incorporated by reference for assisting the enablement of the novel subject matter of the present disclosure. That head mounted display system additionally includes a head mounted display apparatus that is separated from the laser light engine and comprising a display unit that displays laser images. The head mounted display system further includes an imaging device coupled between the remote laser light engine and the head mounted display apparatus. The imaging device creates laser images from the laser light transmitted through an optical cable in accordance with the display signal. The laser images are delivered to the display unit in order to create display images that can be viewed by a user of the head mounted display apparatus.

Figure 9:
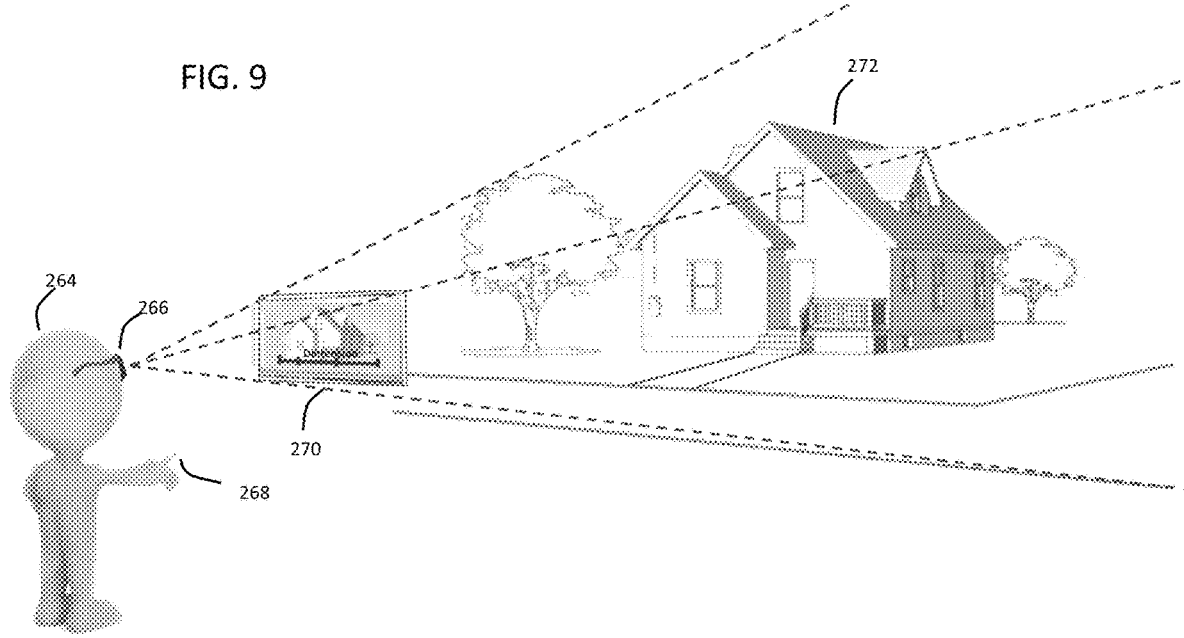
FIG. 9 shows a device user 264 operating AR glasses/transparent screen device with an exemplary 3D/optical sensor system.

FIG. 9, shows a view of device user 264 operating AR glasses/transparent screen device with 3D/optical sensors 266. The device is used to collect optical point registration data for measurement of object 270 for insurance, construction or general purpose. Device user 264 is using a hand gesture to select 268 measurement options on projected AR screen 270. Property 272 is being optically scanned with AR Glasses/Transparent Screen Device 266. AR Glasses/Transparent Screen Device 266 records Data Set for future use.

The present invention relates generally to head-mounted display systems. More particularly, the present invention relates to improved arrangements for processing and displaying images in a head-mounted display system. Thus, within the context of the present disclosure a head-mounted display (HMD) is worn by a person on the head in order to have video information directly displayed in front of the eyes. An HMD for use with the present disclosure may have either one or two small CRT, LCD or OLED displays with magnifying lenses and other associated optical elements. The display(s) and optics are typically embedded in a helmet, glasses, or a visor, which a user can wear. HMDs may be configured as binocular HMDs for dual eye use. HMDs may also be configured as monocular HMDs for single eye use. The arrangement generally depends on the desired needs of the user.

Lenses and other optical components may be used to give the user the perception that the images are coming from a greater distance, to prevent eyestrain. In HMDs that use a single display, the image is typically projected through optics that split the image into two identical images and redirects each image to the respective eye. With two displays, the HMD can show stereoscopic images. The stereoscopic images attempt to create depth to the images by simulating the angular difference between the images viewed by each eye when looking at an object, due to the different positions of the eyes. This angular difference is one of the key parameters the human brain uses in processing images to create depth perception or distance in human vision.

Some HMDs can be used to view a see-through image imposed upon a real-world view, thereby creating what is typically referred to as an augmented reality. This is accomplished by reflecting the video images through partially reflective mirrors, such that the real world is seen through the mirrors' reflective surfaces. The augmented reality can be combined with the stereoscopic images in various types of applications. Some examples include applications in surgery, where radiographic data, such as CAT scans or MRI imaging can be combined with the surgeon's vision. Military, police and firefighters use HMDs to display relevant tactical information, such as maps or thermal imaging data. Engineers and scientists use HMDs to provide stereoscopic views of CAD schematics, simulations or remote sensing applications. Consumer devices are also available for use in gaming and entertainment applications.

In one configuration, the head mounted display includes a remote laser light engine that generates laser light associated with a display signal. The head mounted display also may include a head mounted display apparatus that is separated from the laser light engine and comprising a display unit that displays laser images. The head mounted display further includes an imaging device coupled between the remote laser light engine and the head mounted display apparatus. The imaging device creates laser images from the laser light transmitted through an optical cable in accordance with the display signal. The laser images are delivered to the display unit in order to create display images that can be viewed by a user of the head mounted display apparatus.

In another embodiment, the head mounted display includes a frame wearable on a user's head. The frame includes a viewing area. The head mounted display apparatus also includes one or more imaging devices that are physically decoupled from and in optical communication with a light arrangement. The imaging devices are carried by the frame and configured to create images from light received from the light arrangement in conjunction with a display signal. The head mounted display apparatus further includes a left optical element carried by the frame and positioned at the left of the viewing area. The left optical element is configured to receive images from at least one of the imaging devices and display them on a left imaging surface thereby creating left display images. The head mounted display apparatus additionally includes a right optical element carried by the frame and positioned at the right of the viewing area. The right optical element is configured to receive images from at least one of the imaging devices and display them on a right imaging surface thereby creating right display images. The left and right display images are viewable by a user when the frame is worn on the user's head, and the viewing area is positioned in front of the user's eyes.

The inventive subject matter here presented uses augmented reality glasses to collect data other than augmented reality Applications, the present augmented reality glasses with 3D/optical device sensors digitally record actual sizes and dimensions. This provides for an interaction with real life physical objects, as they may relate to color, texture, weight, size and maneuvering of objects. Moreover, with built-in 3D/optical sensors for data collection of digitized photos with 3D/optical points registration for data collection, these head mounted displays make possible AI applications.

The disclosed subject matter further enables human interaction for color & texture comparison on AR glasses. Also, another AR objects that will need human selection choices. All human assisted decisions on AR glass/AR platform, where humans have to make final decisions due to color, texture against real world environmental differences where present time AI cannot be distinguished; theses AR interaction data is to be stored for future AI application use.

Figure 10:
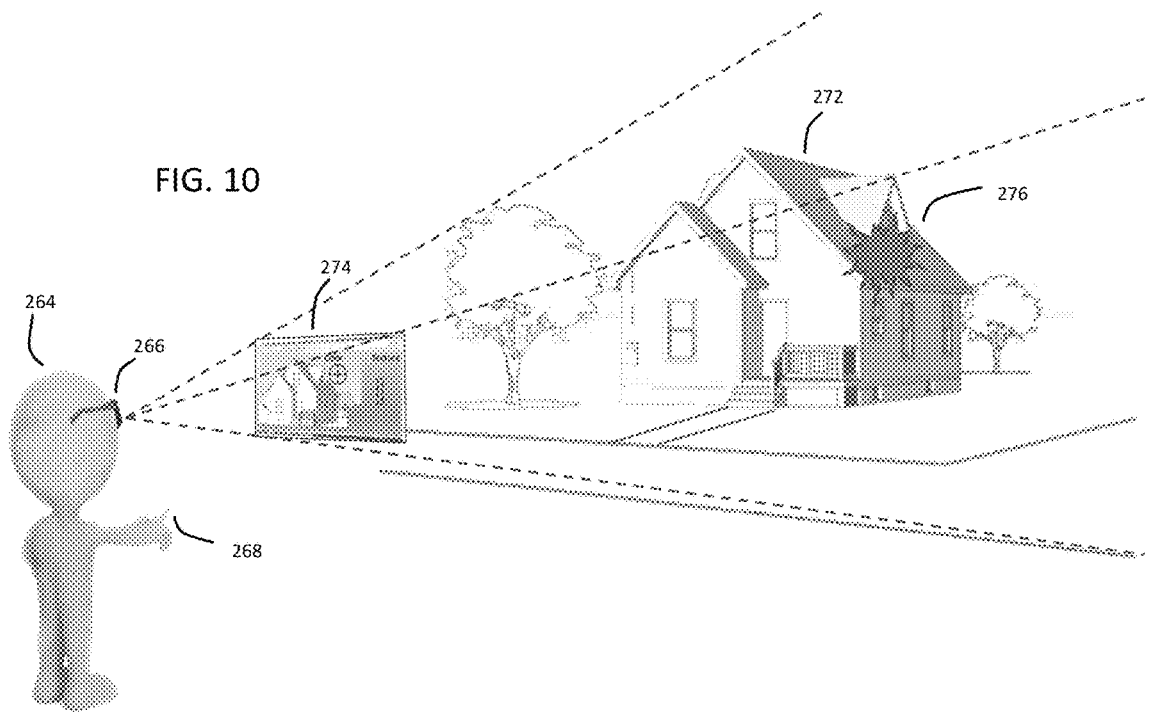
FIGS. 10 and 11 illustrate a user using a pair of glasses with an AR glasses/transparent screen device according to the teachings of the present disclosure.

Here augmented reality glasses include the necessary sensors in conjunction with AI data collection software for recording digital images and 3D/optical sensors measurement. The AR glasses here provided display 2D drawing and or color, texture, images in Augmented Reality Platform by user selected object seen through transparent display screen. For example, FIG. 10, provides a view of device user 264 operating AR glasses/transparent screen device 266. Device 266 collects 3D/optical sensor data, which may include image, size, color, texture, damaged area 276 and any other data capable of AR glasses/transparent screen device 266. Device 266 AR platform uses previous 2D-images taken by non-digital film camera, 2D and or digital image for image correlations 274 of damaged property 272 as insurance, construction or general-purpose comparison/restoration detail. Device User's 264 has available augmented realty menu option selections 268 with real world interactions while using AR glasses/transparent screen device 266 collects data for future use, to include augmented realty human interaction data for accelerated AI machine learning.

Figure 11:
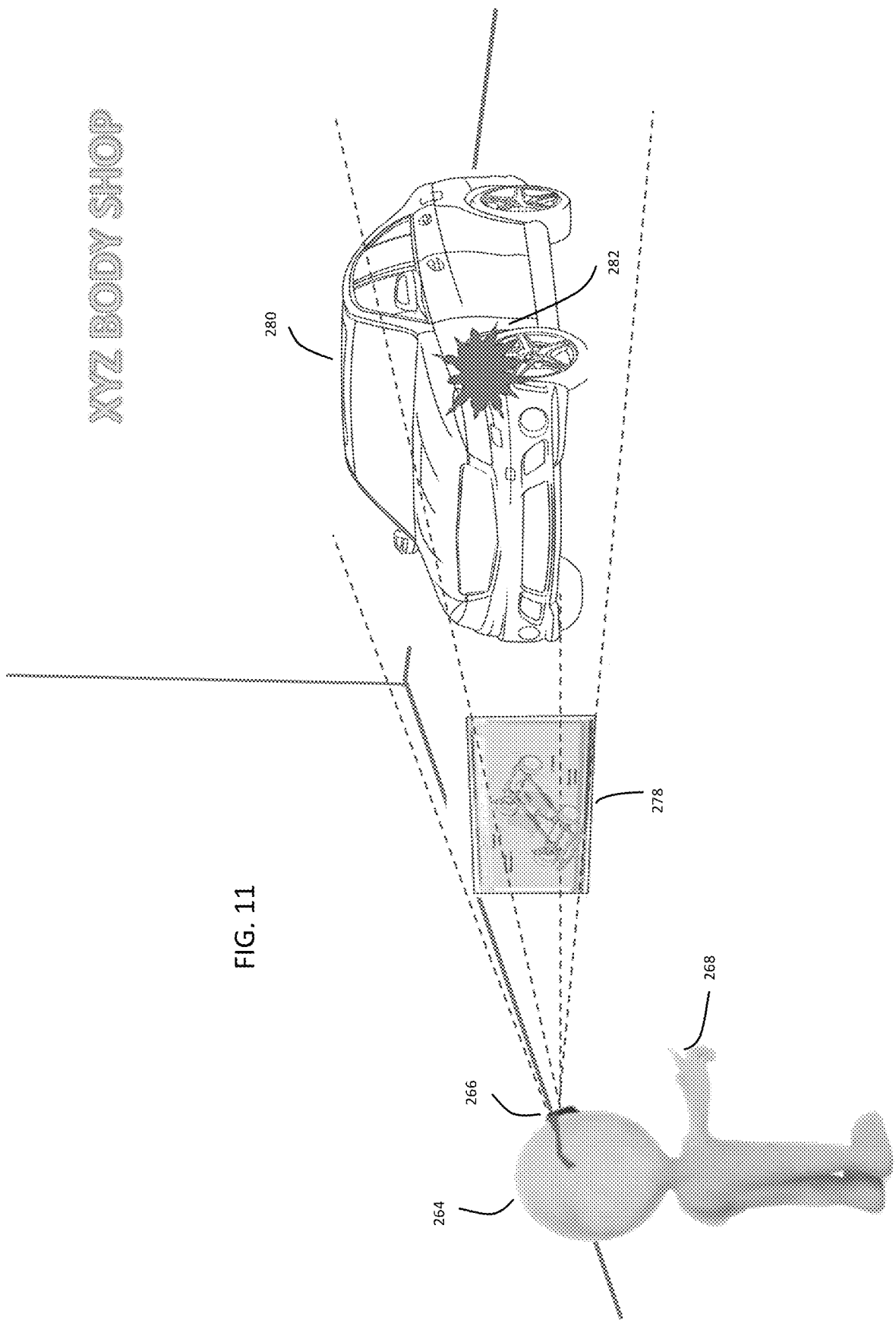

FIG. 11, shows device user 264 operating AR glasses/transparent screen device 266. Device 266 displays 2D image parts diagram 278, which projects onto damaged automotive 280. 2D-image diagram parts 282 are used assist and expedite device user selections. AR glasses/transparent screen device 266 records all data to include Operator's selection 268 for future use. For insurance, construction and other commercial application of image, color and texture correlation on augmented realty glasses/transparent display screen device.

Figure 12:
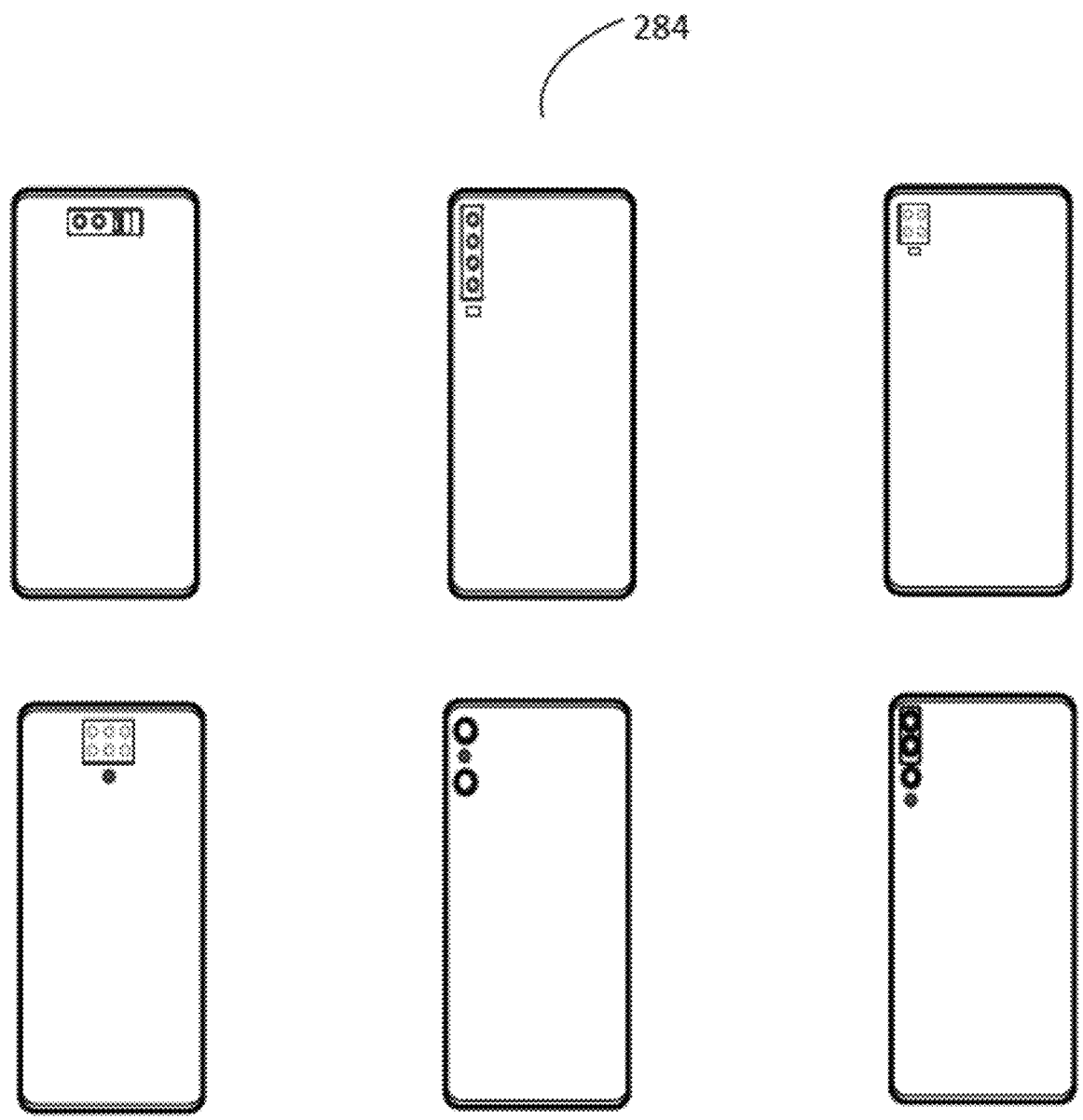
FIG. 12 shows rear view of Mobile Devices with different camera and 3D sensor/3D optical sensor or sensors configurations.

FIG. 12 shows rear view of Mobile Devices with different camera and 3D sensor/3D optical camera sensor or sensors configurations 284.

Figure 13:
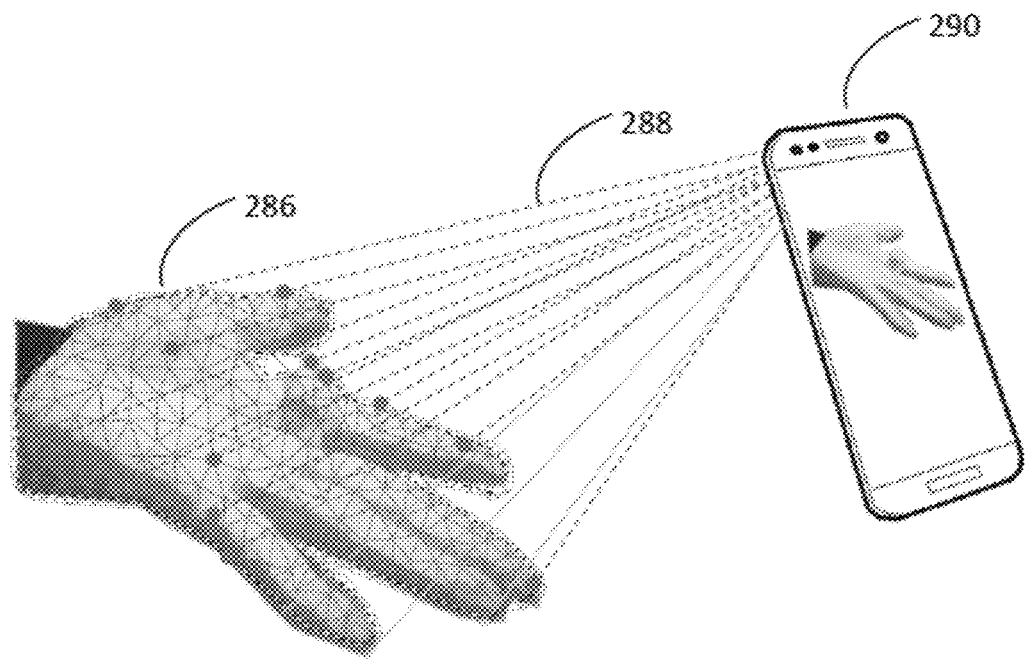
FIG. 13 illustrates Mobile Device with 3D sensor scanning a hand with medical condition multiple times for redundancy.

FIG. 13 illustrates Patient with visible medical condition on the hand 286 being scanned with 3D sensor/3D optical camera 288 with Mobile Device with 3D sensor 290. Scanning of medical condition is performed multiple times and from multiple angles for redundancy 288.

Figure 14:
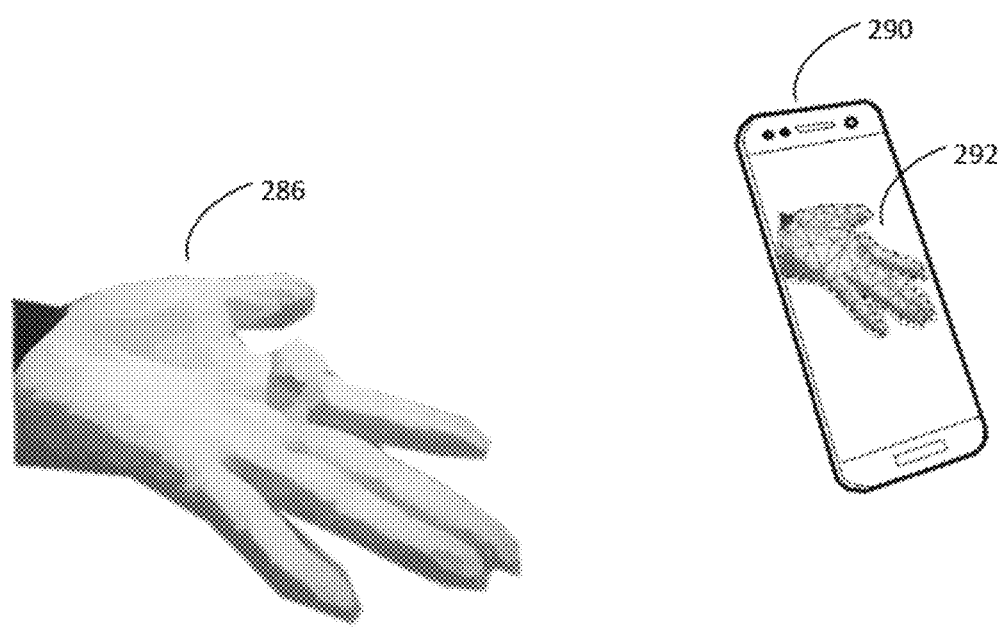
FIG. 14 shows Mobile Device with 3D sensor digitally recording 3D scanned images on Mobile Device screen

FIG. 14 illustrates Patient's hand 286 and Mobile Device with 3D sensor 290 digitally recording 3D scanned images on Mobile Device screen 292.

Figure 15:
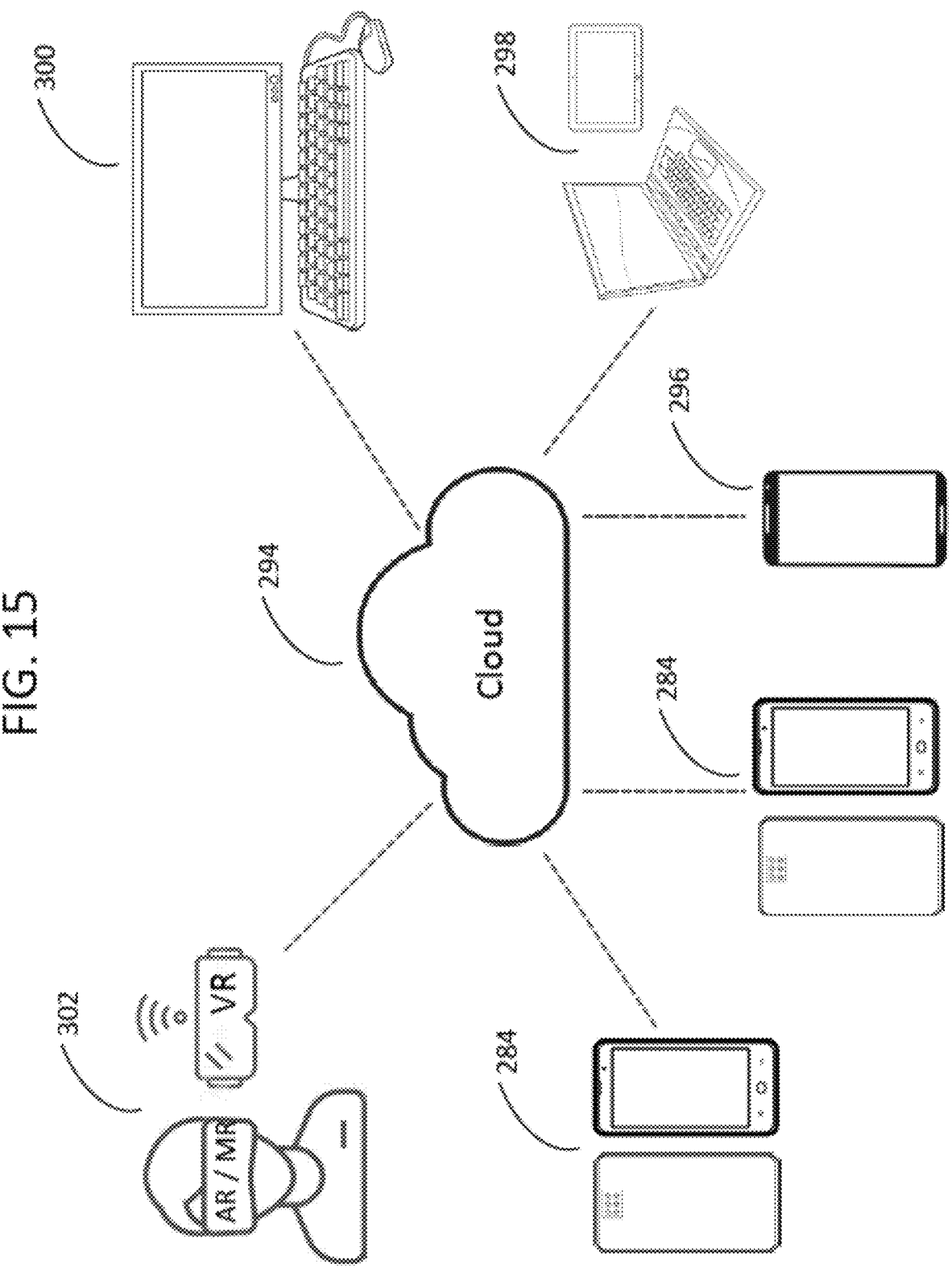
FIG. 15 illustrates Mobile Device with 3D sensor sending data to cloud for sharing to other Screen Devices, to include Mobile Devices with same QMS certified device.

FIG. 15 illustrates Mobile Device with 3D sensor 284 sending data to Internet Cloud 294 for sharing to Mobile Devices with 3D sensor with same QMS certified mobile device 284, transparent display mobile device 296, laptop and tablets 298, desktop PC 300, AR/MR glasses and VR head mounted unit (HMU).

mobile devices and AR/MR/VR glasses head mount unit (HMU) with transparent and non-transparent screen and 3D sensor and or 3D optical camera sensor used for 3D digital scans to capture 3D point registration data for transmission to other display screen devices to include mobile devices for medical practitioner's opinion and diagnosis.

With the use of mobile devices and AR/MR/VR glasses head mount units (HMU) with transparent and non-transparent screen and 3D sensor and or 3D optical camera sensor is used by medical practitioner for telemedicine/medical diagnostic device, telemedicine color and texture analysis quality management system (QMS) is to be established with multiple redundant 3D images from same and different angles for redundancy. While medical QMS shall include management subject matters to include but not limited to: preventive action, advisory notices, recalls, and vigilance, customer complaints, continual improvement, analysis of data, monitoring and measurement of product, corrective action, customer feedback and post market surveillance, internal quality audits, control of monitoring and measuring devices, preservation of product, customer property, control of nonconforming product, identification and traceability, individual work instructions, supplier evaluation, purchasing, design and development, risk management, accident prevention program, work environment and contamination control, information system maintenance schedule, employee training effectiveness review, policies & procedures, competence, awareness & training, organizational chart, QMS planning, customer service survey, customer related processes, management review, control of records, control of documents, regulatory bodies, quality system process interaction picture, validation of software and periodic recertification/validation/audit review of QMS.

U.S. Patent Application Publication US20190050988A1 discloses a method and system for image-based disease diagnostics using a mobile device. The diagnostic system performs disease diagnostic tests using at least an optical property modifying device and a mobile device. A user provides a biological sample from a patient to the optical property modifying device that reacts with a reagent in one or more reaction chambers of the device. The user captures one or more images of the one or more reaction chambers using an optical sensor of the mobile device. The diagnostic system can determine a quality level of the images based on factors such as skew, scale, focusing, shadowing, or white-balancing. Based on an analysis of the captured image, the diagnostic system can determine a test result of a disease diagnostic test for the patient. The diagnostic system may communicate the test result, as well as instructions for the disease diagnostic test, to the user via the mobile device. The full disclosure of U.S. Patent Application Publication US20190050988A1 is expressly incorporated by reference.

US patent application publication 20190110740A1 discloses a system, apparatus and method for assessing wound and tissue conditions. In that disclosure a combination thermal and visual image capturing device used to capture real time thermal and visual images of surface and subsurface biological tissue, said device comprising: a power source, said power source functionally connected to said device; a housing, a long wave infrared microbolometer, said microbolometer functionally connected to said power source a digital camera; a short wave infrared microbolometer, said microbolometer functionally connected to said power source; a digital camera, said digital camera functionally connected to said power source; and a digital camera, said digital camera functionally connected to said power source, wherein said digital camera and 3D camera are contained within a USB peripheral device; said imaging apparatus further comprising means to electronically provide combined thermal image information from the microbolometers and visual image information from said digital camera and said 3D camera to another electronic device. The full disclosure of U.S. Patent Application Publication 20190110740A1 is expressly incorporated by reference.

US patent application publication US20190104939A1 discloses a non-invasive biological, chemical markers and tracers monitoring device in blood including glucose monitoring using adaptive rf circuits and antenna design. That disclosure includes a device that measures glucose concentration in blood without any extraction of blood. The device is a non-invasive method for measuring glucose Radio Frequency and Antenna Circuits and Systems. The device is a wearable device that can non-invasively measure blood glucose levels in an instantaneous manner and continuous manner. The full disclosure of U.S. Patent Application Publication US20190104939A1 is expressly incorporated by reference.

Chinese Patent Application CN108903946A discloses a remote medical detection system and method for remote human body 3D model restoration. The system comprises a detection position, a detector with a detection head, a local detection unit, and a remote detection unit; the local detection unit photographs the 3D data of a detecting object, sends the 3D data to the remote detection unit, drives the detection head to move and/or expand and contract according to the guiding information of the remote detection unit to complete the detection, and forms a detection image; the remote detection unit receives the 3D data and forms a detection object model according to the 3D data remote simulation, operates on the detection object model by the probe positioning device, forms guiding information, and completes local detection in the local detection unit according to the guiding information. The invention also provides a medical detection method. By means of the medical detection system and method of the present invention, detection technicians having detection skill are not required to operate at the local end, and they can perform corresponding detection operations according to the guiding information of the remote end, thereby solving the problem that the medical institution that does not have the detection technician has difficulty in detecting. The full disclosure of Chinese Patent Application Publication CN108903946A is expressly incorporated by reference.

Thus, in the presently disclosed embodiments, augmented reality glasses have built in 3D/optical sensors that insurance programs can harness to collect optical points matching data within the digital picture, recorded from the claims inspector's field of view. Also, during the viewing/recording process, a third party may input an independent opinion. Instead of quarterly QC compliance check, the system allows for real-time reviews while recording. If you use third party inspectors, it would be great audit tool.

Another aspect of the present disclosure includes surveying an object using augmented reality glasses making available physical properties providing color, shape, and texture data in order to meet the user's best judgment of a parts match. For image correlations, such as evaluating property or automotive damages, displaying a simple 2D parts chart, with or without color and texture information, instead of a full 3D Model for quick augmented realty application deployable solution.

AR glasses use 3D/Optical Sensors, and properly configured software may evaluate these data sets to estimate distance measurements without climbing from the ground, an additional safety feature (within distance limitations). AR imaging software assist humans by streamlining the array of selection choices available. Device user and augmented realty glasses collecting data from single digital stereovision point of view. In turn, computers recording real world information add to the AR data sets available, for future Artificial Intelligence Software refinement. Harnessing the capabilities of Augmented Reality Glasses accelerate Artificial Intelligence Learning by providing real-world data sets and observing the human element of the decision-making process.

Data Set using built in sensors on augmented reality glasses/transparent display screen with minimal augmented reality image opaque for 100% to 1% or without any images displayed on transparent display screen for purpose reduction of computer screen eye fatigue and to prolong transparent display screen commercial applications. Use of 2D-image, non-digital camera image and Data Set image correlations used as evaluating damages, with or without color and texture information on transparent display screen device for rapid augmented realty platform deployment of commercial application.

The present disclosure uses augmented reality glasses to collect data other than that useful by known augmented reality applications. This includes 3D/optical device sensors digitally capable of recording actual sizes and dimensions. Moreover, there is here the ability to provide the interaction with real life physical object to color, texture, weight, size and maneuvering of objects. With the presently disclosed subject matter, a new dimension of human interaction for color & texture comparison on AR glasses. These features may permit AR objects to make clear human selection choices. All human assisted decisions on AR glass/AR platform, where humans have to make final decisions due to color, texture against real world environmental differences where present time AI cannot be distinguished; theses AR interaction data is to be stored for future AI application use.

US Patent Application No. 20150234508A1, entitled "Display System for Displaying Augmented Reality Image And Control Method for The Same," filed on Feb. 17, 2014 and claiming priority to Korean Patent Application No. KR10-2014-0017876, discloses a display system that displays, at a first position on the transparent flexible display unit, a first augmented reality object corresponding to a first real object forming a first angle relative to the camera unit, and displays, at a second position on the transparent flexible display unit, a second augmented reality object corresponding to a second real object forming a second angle relative to the camera unit, wherein, upon detecting bending of the transparent flexible display unit, the processor displays the first augmented reality object at a third position spaced a first distance apart from the first position, and displays the second augmented reality object at a fourth position spaced a second distance apart from the second position, wherein, when the first angle is greater than the second angle, the first distance is set to be greater than the second distance. The subject matter and substance US Patent Application Publication No. 20150234508A1 is here expressly and wholly incorporated into the present disclosure in its entirety as may be necessary or desirable for teaching the novel and enabling aspects of the present disclosure US Patent Application No. 20120154441A1, entitled "Augmented Reality Display System And Method for Vehicle," filed on Dec. 12, 2010 and claiming priority to Korean Patent Application No KR10-2010-0129475, discloses a system includes a head front display device, an eye position tracking camera to track movement of a driver's irises, a front view camera to take a picture of a front view of the driver, a head front display device controller to implement at least one of an angle change, forward movement, backward movement, upward movement, downward movement, leftward movement, and rightward movement of the head front display device, an image adjuster to adjust an object displayed on the head front display device in association with an object of an actual view seen through the front window of the vehicle based on positions of the driver's irises obtained through the eye position tracking camera and an image of the front view obtained by the front view camera, and a display unit controlled by the image adjuster and configured to display information on the head front display device. The subject matter and substance US Patent Application Publication No. 20120154441A1 is here expressly and wholly incorporated into the present disclosure in its entirety as may be necessary or desirable for teaching the novel and enabling aspects of the present disclosure.

US Patent Application No. 20130207896A1, entitled "Augmented Reality Display System And Method of Display," filed on Oct. 22, 2010, and claiming priority to Priority to PCT/US2010/053860, discloses a display system that includes a display, including a display screen; a viewpoint assessment component to determine a viewpoint of a user positioned in front of the display screen; and an object tracking component to track the user manipulation of an object positioned behind the display screen. The subject matter and substance US Patent Application Publication No. 20130207896A1 is here expressly and wholly incorporated into the present disclosure in its entirety as may be necessary or desirable for teaching the novel and enabling aspects of the present disclosure.

US Patent Application No. 20020167536A1, entitled "Method, System and Device for Augmented Reality," filed on Mar. 3, 2001, and claiming priority to Priority to UK Patent Application No. GB0107952A, discloses the present invention describes A portable electronic device comprises augmented reality viewing apparatus for viewing a real scene and a superimposed computer-generated overlay scene. In one embodiment the viewing apparatus comprises a display screen (2) and a semitransparent mirror (3). The semitransparent mirror (3) is pivotally mounted on the device and may be rotated between a position for viewing augmented reality and a position for viewing a displayed image alone. In another embodiment the real scene is viewed through a transparent display screen. When viewing augmented reality, the user aligns the overlay scene with the real scene by means of an alignment indicator in the overlay scene which corresponds to a predetermined element of the real scene. The device may be equipped with location determining means (50), the selection of a displayed image thereby being dependent on the location of the device, whether the images for display are stored locally in the device or transmitted by radio from a remote server. The device may also be equipped with an orientation sensor so that the selection of a displayed images is dependent on orientation of the device. The subject matter and substance US Patent Application Publication No. 20020167536A1 is here expressly and wholly incorporated into the present disclosure in its entirety as may be necessary or desirable for teaching the novel and enabling aspects of the present disclosure.

Korean Patent Application No. KR20090047889A, entitled "The Method, Apparatus and System for Realizing Augmented Reality Using Transparent Display," Nov. 8, 2007-11-08 and claiming priority to Korean Patent Application No. KR1020070113970A, discloses the present invention provides relates to an augmented reality implementation, transparent AR implemented without complex electronic devices are required optical structure using the device. Augmented reality implementation method using a transparent electronic device according to an embodiment of the present invention to do this is, (a) recognizing a current position of a user; (B) outputting to the server that stores the image data in accordance with the position of the current position information of the recognized user, and in response to the current position information receiving image data received from the server; (C) recognizing the direction you're looking; And (d) a step of outputting on the screen consisting of a transparent electronic device for transmitting a light inputted partial image data to be displayed to the user of the received video data based on the recognized direction information from the outside. The subject matter and substance Korean Patent Application No. KR20090047889A is here expressly and wholly incorporated into the present disclosure in its entirety as may be necessary or desirable for teaching the novel and enabling aspects of the present disclosure.

US Patent Application No. 20140114530A1, entitled "Vehicle Computer System with Transparent Display," filed on Oct. 19, 2012, and claiming priority to US201261715990P, discloses a vehicle computer system. The vehicle computer system gathers data from a safety sensor to determine whether the proper safety conditions are present for the vehicle operator to interact with the vehicle computer system. A safety controller receives safety condition data gathered from the safety sensor and instructs the display manager to disable the display of information to the vehicle operator during unsafe operating conditions. The vehicle computer system advantageously employs a transparent display screen to provide greater field of vision of the vehicle operator than could be provided by a traditional display screen. The subject matter and substance US Patent Application Publication No. 20140114530A1 is here expressly and wholly incorporated into the present disclosure in its entirety as may be necessary or desirable for teaching the novel and enabling aspects of the present disclosure.

In summary, In summary, here is provided a method and system for comparing and accurately determining the color of a predetermined human body part using an electronic mobile device comprising at least one transparent display screen, the method and system provide the steps and structures for storing optical processing data and optical processing instructions and algorithms in a memory associated with the electronic mobile device. The disclosed method and system enable operating a computer processor associated with the electronic mobile device for executing said optical processing instructions and algorithms in response to optical processing data generated by the electronic mobile device. The disclosed method and system enable directing an optical lens of the electronic mobile device to capture an image of an human body part for display on at least one transparent display screen of the mobile electronic device, wherein said transparent display screen comprises a head-mounted display in the form of a pair of augmented reality glasses, The disclosed method and system enable collecting a first set of optical processing data using data deriving from the capture of the image through the optical lens of the electronic mobile device, said first set of optical processing data comprising a first set of color data. The disclosed method and system enable displaying the human body part for display through a transparent portion of the at least one transparent display screen of the mobile electronic device. The disclosed method and system enable receiving and storing in the memory a second set of color data associated with a perceived color of the human body part for display as perceived through the at least one transparent display screen. The disclosed method and system enable executing instructions on the computer processor associated with the electronic mobile device determining image difference values between said first set of optical processing data and said second set of optical processing data The disclosed method and system enable displaying on the at least one transparent display screen values for said image differences from the group consisting of color differences, texture differences, transparency differences, lighting differences, motion differences, focus differences and the like. The disclosed method and system enable further enhancing the transparent display screen through collection of various information for feedback with utilization of all sensors to include 3D camera and or 3D sensor The system includes optical processing data and optical processing instructions and algorithms for storing in the memory associated with the electronic mobile device and executing on the computer processor associated with the electronic mobile device and executing in response to optical processing data generated by the electronic mobile device said optical processing data and optical processing instructions and algorithms for adjusting the color value of said color of interest of object as perceived through said optical lens of said electronic mobile device. The system further includes optical processing data and optical processing instructions and algorithms for storing in the memory associated with the electronic mobile device and executing on the computer processor associated with the electronic mobile device for executing instructions associated with the optical processing data within an augmented reality computer process using optical processing data in the memory and optical processing instructions and algorithms executing the computer processor associated with the electronic mobile device.

The system uses at least one transparent display screen as a single display screen having at least one bonded monolithic form or a layered monolithic form. This form may take be a head mounted display, such as a pair of augmented reality glasses. The system further includes optical processing data and optical processing instructions and algorithms for storing in the memory associated with the electronic mobile device and executing on the computer processor associated with the electronic mobile device for controllably varying the translucence of said at least one transparent display screen, or augmented reality glasses, through a translucence range of zero translucence or opaque to 100% translucence or transparent. The system further includes optical processing data and optical processing instructions and algorithms for storing in the memory associated with the electronic mobile device and executing on the computer processor associated with the electronic mobile device for generating suggestions to a user for determining possible factors causing a color value for said first perceived color of interest to differ from a color value for said second perceived color of interest. A technical aspect of the present disclosure includes the ability to align the sensors so with the number for if there are multiple surgeries and we have a parallax image. There is the date the ability to go deeper with a hand gesture and to understand how the alignment of the sensors occurs for the x-ray image with the optical image in with the display.

The detailed description set forth herein in connection with the appended drawings is intended as a description of exemplary embodiments in which the presently disclosed subject matter may be practiced. The term "exemplary" used throughout this description means "serving as an example, instance, or illustration," and should not necessarily be construed as preferred or advantageous over other embodiments.

This detailed description of illustrative embodiments includes specific details for providing a thorough understanding of the presently disclosed subject matter. However, it will be apparent to those skilled in the art that the presently disclosed subject matter may be practiced without these specific details. In some instances, well-known structures and devices are shown in block diagram form in order to avoid obscuring the concepts of the presently disclosed method and system.

The foregoing description of embodiments is provided to enable any person skilled in the art to make and use the subject matter. Various modifications to these embodiments will be readily apparent to those skilled in the art, and the novel principlesand subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter.

What is claimed is:

1. A method for comparing and accurately determining the color of a predetermined human body part using an electronic mobile device comprising at least one transparent display screen, the method comprising the steps of: storing optical processing data and optical processing instructions and algorithms in a memory associated with the electronic mobile device; operating a computer processor associated with the electronic mobile device for executing said optical processing instructions and algorithms in response to optical processing data generated by the electronic mobile device; directing an optical lens of said electronic mobile device to capture an image in three dimensions of a human body part for display on at least one transparent display screen of said mobile electronic device, wherein said transparent display screen comprises a head-mounted display in the form of a pair of augmented reality glasses; collecting a first set of optical processing data using data deriving from the capture of the image in three dimensions through said optical lens of said electronic mobile device, said first set of optical processing data comprising a first set of color and three-dimensional texture data; displaying the human body part for display through a transparent portion of said the at least one transparent display screen of the mobile electronic device; receiving and storing in said memory a second set of color and three-dimensional texture data associated with a perceived color and perceived three-dimensional texture of the human body part for display as perceived through said at least one transparent display screen; executing instructions on said computer processor associated with said the electronic mobile device for determining image color and three-dimensional texture difference values between said first set of optical processing data and said second set of optical processing data; displaying on said at least one transparent display screen values for said image color and three-dimensional texture differences from the group consisting of color differences, texture differences, transparency differences, lighting differences, motion differences, and focus differences; and further enhancing said the transparent display screen through collection of various information for feedback with utilization of all sensors to include 3D camera and or 3D sensor; and further displaying matching color and three-dimensional texture samples for selection by a user for matching according to said image difference values using three-dimensional and parallax touchscreen operation for distinguishing pressure differences in touch screen control according to variations in color and three-dimensional texture; further displaying matching three-dimensional texture samples for selection by a user for matching according to said image difference values; continuing to receive user selections of said matching color images and said matching three-dimensional texture samples according to said texture difference values according to control inputs from a user; and completing selection of said matching color images and said matching three-dimensional texture samples until receiving a cycle completed input into said computer processor.

2. The method of claim 1, further comprising the step of transmitting said image difference values to a telemedicine treatment practitioner for facilitating telemedicine diagnosis and treatment relating to said human body part.

3. The method of claim 1, further comprising the step of receiving optical processing data and optical processing instructions and algorithms in said memory associated with the electronic mobile device and executing on said computer processor associated with said electronic mobile device for executing in response to optical processing data generated by said electronic mobile device said optical processing data and optical processing instructions and algorithms for adjusting the color value of said color of interest and texture value of a three-dimensional texture of interest of object as perceived through said optical lens of said electronic mobile device.

4. The method of claim 1, further comprising the step of receiving optical processing data and optical processing instructions and algorithms in the memory associated with said electronic mobile device and executing on said computer processor associated with said electronic mobile device for executing instructions associated with said optical processing data within an augmented reality computer process using said optical processing data in said memory and said optical processing instructions and algorithms executing on said the computer processor associated with said electronic mobile device.

5. The method of claim 1, wherein said at least one transparent display screen comprises a single display screen having at least one bonded monolithic form.

6. The method of claim 1, wherein said at least one transparent display screen comprises a layered monolithic form.

7. The method of claim 1, further comprising the step of controllably varying the translucence of said at least one transparent display screen through a translucence range of zero translucence or opaque to 100% translucence or transparent.

8. The method of claim 1, further comprising the steps of generating suggestions to a user for determining possible factors causing a color value for said first perceived color of interest and/or a three-dimensional texture value to differ from a color value and/or a three-dimensional texture value for said second perceived color of interest and/or three-dimensional texture of interest.

9. The method of claim 1, wherein an object of interest comprises a tinted translucent liquid or solid object and further wherein said color of interest responds to translucence difference associated with the background against which electronic mobile device images said translucent liquid or solid object.

10. A system for operation on a mobile electronic device comprising at least one transparent display screen for comparing and accurately determining the color and three-dimensional texture of a predetermined human body part for telemedicine diagnosis and treatment, the system comprising:

a memory associated with said electronic mobile device for storing optical processing data and optical processing instructions and algorithms;

a computer processor associated with said the electronic mobile device for executing said optical processing instructions and algorithms and operating in response to optical processing data generated by said electronic mobile device;

an optical lens of said electronic mobile device for directing and capturing an image of an object for display on at least one transparent display screen of said mobile electronic device;

a first set of optical processing data collected using data deriving from the capture of a human body part image for telemedicine diagnosis and treatment through said optical lens of the electronic mobile device, said first set of optical processing data comprising a first set of color and three-dimensional texture data;

a transparent portion of the at least one transparent display screen of the mobile electronic device for displaying the human body part for display;

a second set of color data associated with a perceived color and/or three-dimensional texture of the human body part for receiving and storing in said memory and displaying as perceived through the at least one transparent display screen, wherein said transparent display screen comprises a head-mounted display in the form of a pair of augmented reality glasses;

instructions for executing on said computer processor associated with said electronic mobile device and determining image difference values between said first set of optical processing data and said second set of optical processing data;

a display on a portion on the at least one transparent display screen for indicating said image difference values from the group consisting of color differences, three-dimensional texture differences, transparency differences, lighting differences, motion differences, and/or focus differences;

a 3D camera and/or 3D for further enhancing the transparent display screen through collection of various information for feedback and further a plurality of matching color and three-dimensional texture samples for selection by a user for matching according to said image difference values using three-dimensional and parallax touchscreen operation for distinguishing pressure differences in touch screen control according to variations in color and three-dimensional texture;

a plurality of matching texture samples for further displaying to a user for matching according to said image difference values; and circuitry associated with said computer processor for receiving a cycle completed input for completing said selection.

11. The system of claim 10, further comprising instructions for transmitting said image difference values to a telemedicine treatment practitioner for facilitating telemedicine diagnosis and treatment relating to said human body part.

12. The system of claim 10, further comprising optical processing data and optical processing instructions and algorithms for storing in said memory associated with said electronic mobile device and executing on said computer processor associated with said electronic mobile device and executing in response to optical processing data generated by said electronic mobile device said optical processing data and optical processing instructions and algorithms for adjusting the color value of a color of interest of object and/or three-dimensional texture value of a three-dimensional texture of interest as perceived through said optical lens of said electronic mobile device.

13. The system of claim 10, further comprising optical processing data and optical processing instructions and algorithms for storing in said memory associated with said electronic mobile device and executing on said computer processor associated with said electronic mobile device for executing instructions associated with said optical processing data within an augmented reality computer process using optical processing data in said memory and optical processing instructions and algorithms executing on said computer processor associated with said electronic mobile device.

14. The system of claim 10, wherein said at least one transparent display screen comprises a single display screen having at least one bonded monolithic form, wherein said transparent display screen comprises a head-mounted display in the form of a pair of augmented reality glasses.

15. The system of claim 10, wherein said at least one transparent display screen comprises a layered monolithic form.

16. The system of claim 10, further comprising optical processing data and optical processing instructions and algorithms for storing in said memory associated with said electronic mobile device and executing on said computer processor associated with said electronic mobile device for controllably varying the translucence of said at least one transparent display screen through a translucence range of zero translucence or opaque to 100% translucence or transparent.

17. The system of claim 10, further comprising instructions and data for executing on said computer processor associated with said electronic mobile device for providing a quality management system (QMS) on said mobile device with 3D sensor for using said mobile electronic device as medical device for telemedicine.

18. A system for comparing and accurately determining the color and three-dimensional texture value of a predetermined object, the system comprising:
- a plurality of objects for perceiving color differences, texture differences, transparency differences, lighting differences, motion differences, and/or focus differences; and
- a mobile electronic device comprising at least one transparent display screen, wherein said transparent display screen comprises a non-transparent display screen, bendable display screen and multiple display screens with 3D sensors used as telemedicine, said mobile electronic device further comprising:
    - a memory associated with said electronic mobile device for storing optical processing data and optical processing instructions and algorithms;
    - a computer processor associated with said electronic mobile device for executing said optical processing instructions and algorithms and operating in response to optical processing data generated by said electronic mobile device;
    - an optical lens of said electronic mobile device directing and capturing an image of an object for display on at least one transparent display screen of said mobile electronic device;
    - a first set of optical processing data collected using data deriving from the capture of the image through the optical lens of said electronic mobile device, said first set of optical processing data comprising a first set of color data;
    - a transparent portion of said at least one transparent display screen of said mobile electronic device for displaying the object for display; and
    - a second set of color data associated with a perceived color and/or three-dimensional texture of the object for receiving and storing in said memory and displaying as perceived through the at least one transparent display screen;
    - instructions for executing on said computer processor associated with said electronic mobile device and determining image difference values between said first set of optical processing data and said second set of optical processing data;
    - a display on a portion on said at least one transparent display screen for indicating said image difference values from the group consisting of color differences, texture differences, transparency differences, lighting differences, motion differences, and/or focus differences; and
    - a 3D camera and/or 3D for further enhancing said transparent display screen through collection of various information for feedback and further;
    - a plurality of matching color and three-dimensional texture samples for selection by a user for matching according to said image difference values using three-dimensional and parallax touchscreen operation for distinguishing pressure differences in touch screen control according to variations in color and three-dimensional texture;
    - a plurality of matching three-dimensional texture samples for further displaying to a user for matching according to said image difference values; and
    - circuitry associated with said computer processor for receiving a cycle completed input for completing said selection.

19. The system of claim 18, wherein said mobile electronic device further comprises optical processing data and optical processing instructions and algorithms for storing in said memory associated with said electronic mobile device and executing on said computer processor associated with said electronic mobile device and executing in response to optical processing data generated by said electronic mobile device, said optical processing data and optical processing instructions and algorithms for adjusting the color value of said color of interest and/or a three-dimensional texture value of object as perceived through said optical lens of said electronic mobile device.

20. The system of claim 18, wherein said mobile electronic device further comprises instructions and data for executing on the computer processor associated with said electronic mobile device for providing a quality management system (QMS) on said mobile device with 3D sensor for using said mobile electronic device as medical device for telemedicine.

* * * * *